(12) United States Patent
Park et al.

(10) Patent No.: US 12,049,570 B2
(45) Date of Patent: Jul. 30, 2024

(54) PHOTO-CURABLE BIOINK TO FABRICATE ULTRA-STRONG, ELECTROCONDUCTIVE, AND BIOCOMPATIBLE HYDROGEL FOR REGENERATIVE MEDICINE

(71) Applicant: INDUSTRY ACADEMIC COOPERATION FOUNDATION, HALLYM UNIVERSITY, Chuncheon-si (KR)

(72) Inventors: Chan Hum Park, Chuncheon-si (KR); Young Jin Lee, Seosan-si (KR); Olatunji Abolarin Ajiteru, Chuncheon-si (KR); Ok Joo Lee, Chuncheon-si (KR); Ji Seung Lee, Bucheon-si (KR); Han Na Lee, Chuncheon-si (KR); Md Tipu Sultan, Chuncheon-si (KR); Jang Min Kim, Chuncheon-si (KR); Oh Jun Kwon, Namyangju-si (KR); Ji Ye Kim, Wonju-si (KR); Ji Won Heo, Chuncheon-si (KR); Soon Hee Kim, Chuncheon-si (KR)

(73) Assignee: INDUSTRY ACADEMIC COOPERATION FOUNDATION, HALLYM UNIVERSITY, Chuncheon-si (KR)

( * ) Notice: Subject to any disclaimer, the term of this patent is extended or adjusted under 35 U.S.C. 154(b) by 0 days.

(21) Appl. No.: 17/817,772

(22) Filed: Aug. 5, 2022

(65) Prior Publication Data

US 2024/0026182 A1   Jan. 25, 2024

(30) Foreign Application Priority Data

Jul. 22, 2022   (KR) .................. 10-2022-0091120

(51) Int. Cl.
| | | |
|---|---|---|
| *C09D 151/08* | (2006.01) | |
| *A61L 27/22* | (2006.01) | |
| *A61L 27/26* | (2006.01) | |
| *A61L 27/50* | (2006.01) | |
| *A61L 27/52* | (2006.01) | |
| *B33Y 70/00* | (2020.01) | |
| *C08F 289/00* | (2006.01) | |
| *C09D 5/24* | (2006.01) | |
| *C12N 5/00* | (2006.01) | |
| *C12N 5/077* | (2010.01) | |
| *C12N 5/079* | (2010.01) | |

(52) U.S. Cl.
CPC .......... *C09D 151/08* (2013.01); *A61L 27/222* (2013.01); *A61L 27/26* (2013.01); *A61L 27/50* (2013.01); *A61L 27/52* (2013.01); *B33Y 70/00* (2014.12); *C08F 289/00* (2013.01); *C09D 5/24* (2013.01); *C12N 5/0062* (2013.01); *C12N 5/0068* (2013.01); *C12N 5/0618* (2013.01); *C12N 5/0658* (2013.01); *C12N 2513/00* (2013.01); *C12N 2533/30* (2013.01); *C12N 2533/54* (2013.01); *C12N 2539/00* (2013.01)

(58) Field of Classification Search
CPC ....... C09D 151/08; C09D 5/24; A61L 27/222; A61L 27/26; A61L 27/50; A61L 27/52; C08F 289/00; C12N 2513/00; C12N 2533/30; C12N 2533/54; C12N 2539/00
See application file for complete search history.

(56) References Cited

FOREIGN PATENT DOCUMENTS

| CN | 110003392 B | 9/2021 |
|---|---|---|
| KR | 10-2180865 B1 | 11/2020 |
| WO | 2018-186611 A2 | 10/2018 |

OTHER PUBLICATIONS

Shin, S. R., et al., "Cell-Iaden Microengineered and Mechanically Tunable Hybrid Hydrogels of Gelatin and Graphene Oxide," Adv. Mater. 2013, 25, 6385-6391. (Year: 2013).*

Li, X., et al., "Fabrication of Highly Crosslinked Gelatin Hydrogel and Its Influence on Chondrocyte Proliferation and Phenotype," Polymers (Basel) 9(8): 309. doi: 10.3390/polym9080309. (Year: 2017).*

Olate-Moya, F., et al., "Chondroinductive Alginate-Based Hydrogels Having Graphene Oxide for 3D Printed Scaffold Fabrication," ACS Appl. Mater. Interfaces 2020, 12, 4343-4357. (Year: 2020).*

Van Den Bulcke, A. I., et al., "Structural and Rheological Properties of Methacrylamide Modified Gelatin Hydrogels," Biomacromolecules 2000, 1, 31-38. (Year: 2000).*

(Continued)

*Primary Examiner* — Robert M Kelly
*Assistant Examiner* — Eric J Rogers
(74) *Attorney, Agent, or Firm* — Studebaker & Brackett PC

(57) ABSTRACT

The present disclosure relates to the composition and process for the production of an ultra-strong, biocompatible, electroconductive, and stretchable hydrogel, which comprises: a step (a) of physical or chemical modification of natural polymers e.g., preparation of silk nanofiber and double methacrylation of gelatin; a step (b) of graphene oxide (GO) carboxylation; a step (c) of carbodiimidation between methacrylated natural polymers of step (a) and carboxylated GO of step (b); and a step (d) of three dimensional (3D) bioprinting of step (c) with/without silk nanofiber. It was found that these steps in this disclosure give rise to a biocompatible hydrogel with high mechanical strength in the range of load-bearing soft tissue such as tendon and heart as opposed to conventional hydrogels.

3 Claims, 34 Drawing Sheets

(56) References Cited

OTHER PUBLICATIONS

Yu, S., et al., "Facile room-temperature synthesis of carboxylated graphene oxide-copper sulfide nanocomposite," Scientific Reports 5:1 (2015) 16369. doi: 10.1038/srep16369. (Year: 2015).*

Parsamehr, P., S., et al., "Preparation of novel cross-linked graphene oxide membrane for desalination applications using (EDC and NHS)—activated graphene oxide and PEI," Desalination 468 (2019) 114079. (Year: 2019).*

* cited by examiner

10%

20%

30%

PHOTO-CURABLE BIOINK TO FABRICATE ULTRA-STRONG, ELECTROCONDUCTIVE, AND BIOCOMPATIBLE HYDROGEL FOR REGENERATIVE MEDICINE

CROSS REFERENCE TO RELATED APPLICATION

The present application claims priority to Korean Patent Application No. 10-2022-0091120, filed on Jul. 22, 2022, the entire contents of which is incorporated herein for all purposes by this reference.

TECHNICAL FIELD

The present disclosure relates to the functionalization of natural polymers to create a photo-curable bioink that is digital light processing (DLP) printable to ultra-strong, stretchable, electroconductive, and biocompatible hydrogel suitable for the regeneration of load-bearing electrosensitive tissues.

This disclosure is supported financially as followed.
[Project No.] HI20C0408
Ministry of Health and Welfare, Korea Health Industry Development Institute
Advanced medical technology development, "Development of stem cell intra-nasal delivery method and enhancement hydrogel to overcome the obstacles of the stem cell therapy for brain disease" (2020 Apr. 23~2022 Dec. 31)

BACKGROUND ART

The field of tissue engineering uses cells, biomaterials, and physicochemical factors for the regeneration of human tissues. Much has been done to model several biomaterials into the native extracellular matrix (ECM) regarding tissue-specific mechanical cues and cellular support systems. One of such is a hydrogel. The high resemblance of hydrogel to ECM in terms of structural and physical properties cannot be overemphasized. Hydrogels are highly absorbent, cross-linked, and hydrophilic polymers that do not dissolve in water, thereby maintaining their well-defined structures. Hydrogel holds a large amount of water and heterogenous cross-linking points in their structures. Therefore, not usually considered a substitute for load-bearing native soft tissues. When highly swollen, hydrogels lack toughness, strength, elongation, and recoverability. Hence, tissue engineering of load-bearing soft tissues such as cartilage, skin, muscles, heart valves, blood vessels, and tendons is very challenging when using hydrogels. Besides, ECM stiffness has been shown to regulate DNA repair efficiency and genotoxicity sensitivity thereby underscoring the importance of scaffold mechanical similarity to the targeted native tissue. Following these, efforts have been devoted to fabricating elastic and ultra-strong hydrogels by manipulating the chemical networks of hydrogel matrix and using biocomposites such as graphene oxide (GO) biocomposites. While the former usually leads to the reduced water content of the hydrogel, the latter usually leads to brittleness and fracture. However, covalently linking biocomposites to polymer backbones improves their mechanical properties.

The use of synthetic and natural polymers to mimic ECM has been widely exploited in regenerative medicine. Synthetic polymers are easy to functionalize but hard to degrade by natural processes and often lack the cell-interactive motif needed for material integration with the surrounding tissues during implantation. On the other hand, natural polymers like gelatin and silk fibroin (SF) are easily degradable by the biological process but difficult to functionalize. Because of the difficulty in functionalizing natural polymers relative to synthetic polymers, the fabrication of ultra-strong hydrogel from natural polymers remains a challenging study. SF and gelatin are natural polymers that have been widely used as scaffolds for soft tissue engineering. Their biocompatibility and presence of amino side chain in their lysine amino acid residue have been explored in tissue engineering for ease of fabrication and in vivo studies. While SF-based hydrogel has been widely adjudged to have a superior mechanical strength to gelatin hydrogel, its strength is adduced to the β-sheet formation under appropriate stimuli. Moreso, SF nanofiber like other nanoparticles such as GO and iron oxide (IO) has been applied to improve the mechanical strength of the scaffold. Notwithstanding, hydrogel derived from silk nanofiber has not been widely applied for load-bearing ECM substitutes.

Aside from application as a load-bearing ECM substitute, electrically conductive ultra-strong hydrogels are highly desirable for electronic applications such as soft sensors, wearable electronics, and encapsulation of electrosensitive cells for injured brain repair. Covalent reduction of GO has been shown to confer electrical activities to SF hydrogel composites. Enabling silk hydrogel to transcend from semi-conductive to electrically conductive hydrogel. We already disclosed that the electroconductivity of hydrogel has been shown to affect cell-cell communication, cell differentiation, and overall tissue functionality (KR 10-2180865). Biocompatible and photocurable bioink is an important tool for cell encapsulation and drug delivery to delicate tissues. Their viscoelastic property after being transformed to hydrogel protects the encapsulated cells. Their time-dependent degradation ensured the gradual release of their contents after implantation. And their low reactivity ensures the chemical stability of the chemical substance encapsulated in them.

Fabrication of biocomposite into 3D structures has been widely disclosed KR 10-2180865 B 1. Vat polymerization is a commonly used additive manufacturing process because of its high efficiency and resolution. Of all the vat polymerization additive manufacturing processes, DLP stands out with a long service life light source, improved speed, and precision due to its layer-by-layer printing pattern using micro-mirror array devices. Therefore, hydrogel printed from photocurable polymers via a DLP bioprinter has been extensively applied in tissue engineering WO 2018-186611 A2.

Some earlier 3D printing of biocomposite and ultra-strong hydrogel using GO, SF, or gelatin have been disclosed by CN110003392. Generally, most concepts employed in these disclosures are not suitable for cell encapsulation due to their harsh processing conditions. In contrast, the processes employed herein have been shown in related studies to be subtle and suitable for cell encapsulation. Coupled with the strong mechanical property achieved, the application of ultra-strong hydrogel has been widened to include tissue engineering of load-bearing organs.

DISCLOSURE

Technical Problem

The specificity of ECMs to their related tissues necessitates tailoring fabricated hydrogels to match their mechanical, chemical, physical, and electrical properties for successful tissue fabrication.

One objective of the present disclosure is to provide solutions to the major undesirable characteristic of hydrogel that hampered its suitability as a substitute for load-bearing ECM. This problem borders on hydrogel's poor mechanical properties that are usually below 1 MPa due to the high percentage of water. Hence, hydrogels lack recoverability even at low stress as opposed to in vivo ECM they seek to mimic. Secondly, engineering load-bearing electrosensitive tissue such as the heart and muscles requires an increased electrical conductivity of substituent matrix absence of which cell-cell communication, cell differentiation, and overall tissue functionality will be distorted. Lastly, the fabrication of complex hydrogel structure to mimic their counterpart in vivo is cumbersome and often lack repeatability. Consequently, cells and drug deliveries to injured sites and delicate tissues such as the brain has been largely elusive.

Technical Solution

One embodiment of the present disclosure relates to natural polymers (SF and gelatin) used to fabricate the hydrogel. SF and gelatin possess cell-interactive motifs, biocompatible, cheap, and biodegradable. Moreso, the fabrication involved processes that are cytocompatible. Solvents and chemicals used in this disclosure are easily removed and are not cytotoxic both in vitro and in vivo.

In this work, different chemically modified natural polymers were rejigged to improve their mechanical property such that they are fit to be used as a hydrogel for strain-bearing soft tissues such as heart muscles. The fabrication processes that involved GO reduction can introduce electrical properties to the bioink. Another embodiment disclosed herein is photo-curability which can ensure easy cell transplantation and drug delivery to electro-sensitive tissues such as the brain during injury. The fabricated hydrogel structure thereby satisfies the mechanical and electrical similarities to load-bearing electro-sensitive tissues' ECM such as cardiac and brain tissues.

Advantageous Effects

The present disclosure addresses the aforementioned drawback of hydrogel properties by providing composition and manufacturing techniques of ultra-strong hydrogel (GelGOMA and its derivatives) by DLP printing. In general, the present disclosure provides sponge fabrication, bioink composition, biocompatible 3D printed hydrogel, and application of the hydrogel thereof. To bypass the limitations of weak hydrogels described above, the gelatin natural polymer was double methacrylated to improve the crosslinking networks during photopolymerization. And SF nanofiber was prepared to improve the mechanical properties of double methacrylated gelatin. Furthermore, GO with an abundance hydroxyl functional group was carboxylated in preparation for improved conjugation with the double methacrylated gelatin (GelMAGMA).

In an aspect, the present disclosure provides a method for double methacrylation of gelatin which includes a) gelatin reaction with methacrylate anhydride (MA) and b) singly methacrylated gelatin reaction with glycidyl methacrylate (GMA).

In an instance, the gelatin directly reacts with GMA to give GelGMA, a photocurable polymer. The extra amino functional group in GelMAGMA was covalently linked to carboxylated GO through the carboxyl functional group of GO via esterification reaction. This procedure conferred electrical properties on GelGOMA via delocalization of λ-orbital that resulted from the removal of oxygen molecules.

In another aspect, the concentration of linked GO was optionally varied to GelGOMA01, GelGOMA02, and GelGOMA03. The method can optionally include freezing and lyophilization after removal of unreacted substance via dialysis to obtain sponge samples. These methods also include the introduction of a photo-crosslinker to the sponge solution and DLP printing into a strong stretchable and electroconductive hydrogel.

One advantage of the present disclosure is to provide biocompatible 3D printed stretchable and complex structures. Owing to the high degree of crosslinking and SF nanofiller, the printed structures have high mechanical strength. The photocurability of the bioink disclosed herein ensured easy encapsulation of cells and drugs for safe delivery to tissues. Another advantage of some aspect is the electroconductivity of the printed GelGOMA which widen the field of application to the regeneration of electrosensitive tissues. These and other features of GelGOMA of the present disclosure will become apparent from the detailed description of the preferred embodiments when viewed in conjunction with the accompanying drawings.

DETAILED DESCRIPTION

The goal of this disclosure was to solve the disadvantages of the physical properties of naturally-derived polymers when fabricated into hydrogels. Described herein is a process for obtaining ultra-strong hydrogel based on double methacrylation of gelatin, use of natural polymer as nanofillers, and improving the electrical conductivity of polymer with chemically linked GO.

Figure 1:
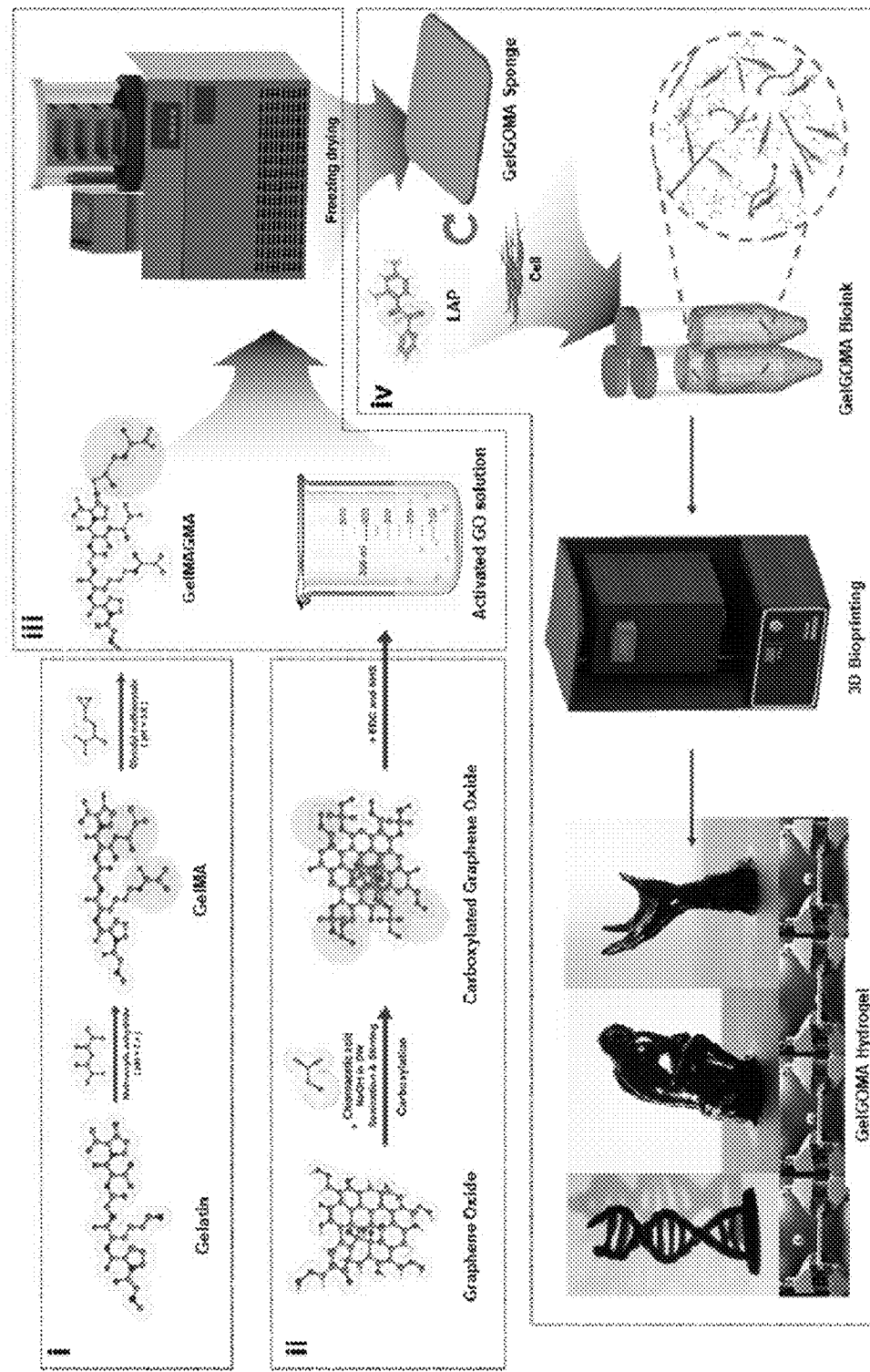
FIG. 1 is a schematic representation of the fabrication processes of the ultra-strong, stretchable, and electroconductive hydrogel. (i) The synthesis of the photocurable gelatin polymer backbone (GelMAGMA) through a double methacrylation process, first with methacrylate anhydride (MA) and later with glycidyl methacrylate (GMA). (ii) Activation of graphene oxide (GO) involving carboxylation that increases the number of carboxyl functional groups on GO and the subsequent activation of the carboxyl groups. (iii) Carbodiimidation reaction between activated GO solution and double methacrylated gelatin (GelMAGMA) to give GelGOMA sponge. (iv) Fabrication of GelGOMA hydrogel via DLP bioprinting to give complex structures of ultra-strong, stretchable, and electroconductive hydrogel (GelGOMA).
Figure 2A:
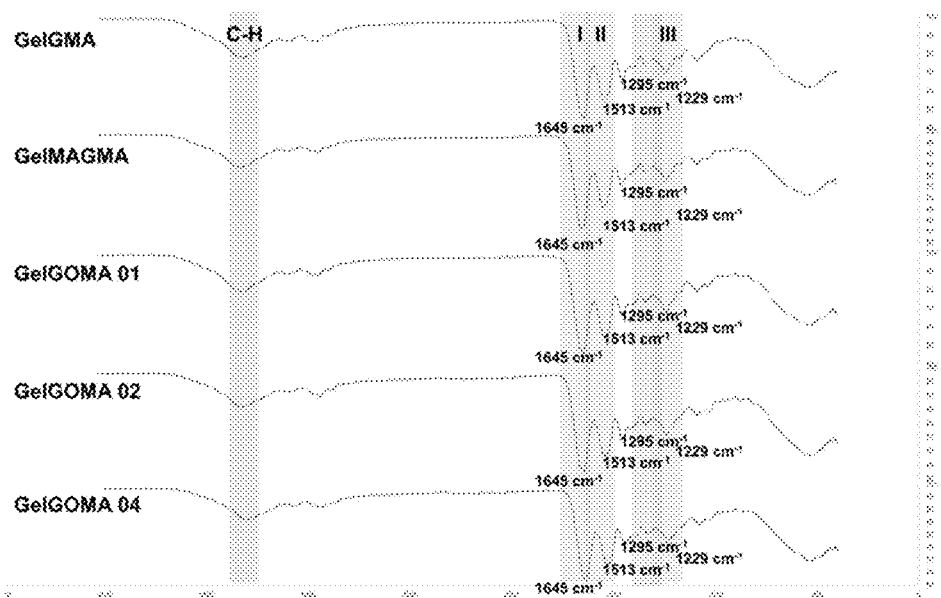
FIG. 2A is the chemical characterization of GelGOMA and related sponges via FT-IR spectra and FIG. 2B is the chemical characterization of GelGOMA and related sponges via $^1$H-NMR.
Figure 2B:
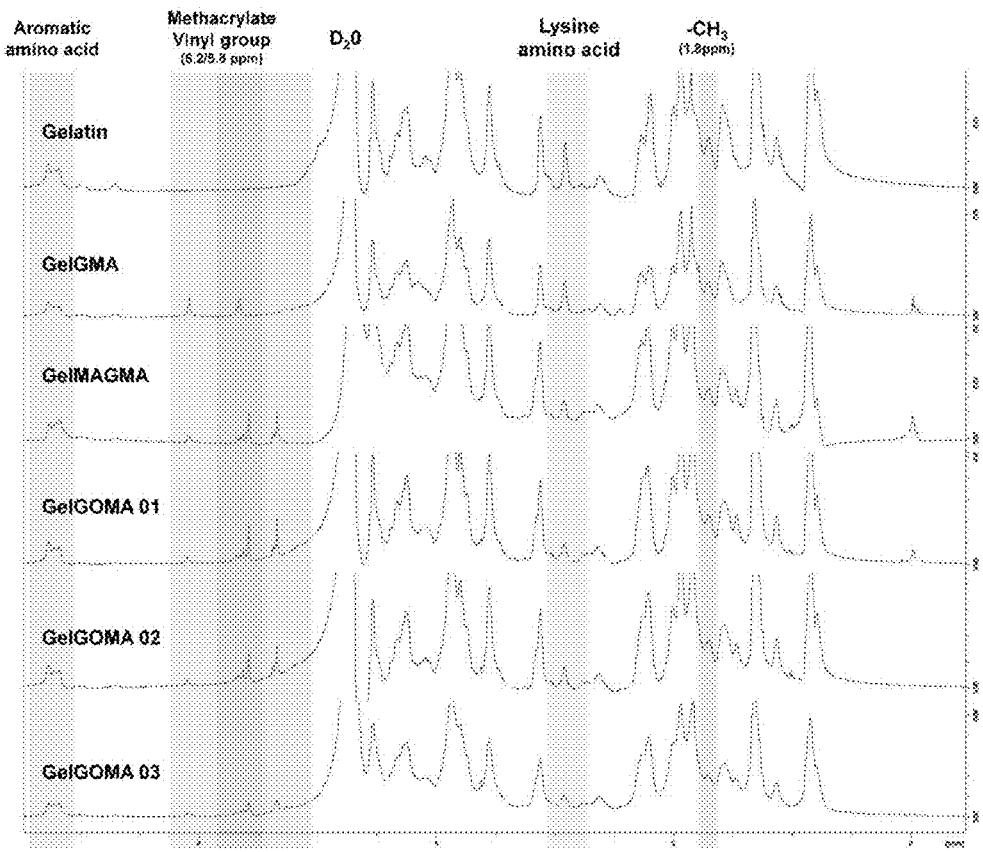

Gelatin has amino, hydroxyl, and carboxyl functional groups that can be used for chemical modification. After the reaction of the amino groups of the gelatin molecule with MA, the remaining hydroxyl and carboxyl groups can be used for further modification in an acidic environment with GMA. From FIG. 1, GelMA macromer was first synthesized, and then GelMAGMA was synthesized using GelMA macromere solution. Following FIG. 2, FT-IR spectra showed the presence of distinct amides I, II, and III at 1645, 1513, and 1229 $cm^{-1}$, respectively. In the methacrylated samples, a new absorption peak at approximately 1295 $cm^{-1}$ suggests the presence of a C—N amide bond. The binding of GMA to gelatin was confirmed by a decrease in the lysine residue signal at $\delta=2.9$ ppm and an increase in the methacrylate vinyl group signal at $\delta=6.2$-6 and 5.8-5.6 ppm. The methyl group signal appeared at $\delta=1.8$ ppm. The protons of the methacrylate group are indicated in the $^1$H-NMR spectrum.

Figure 3:
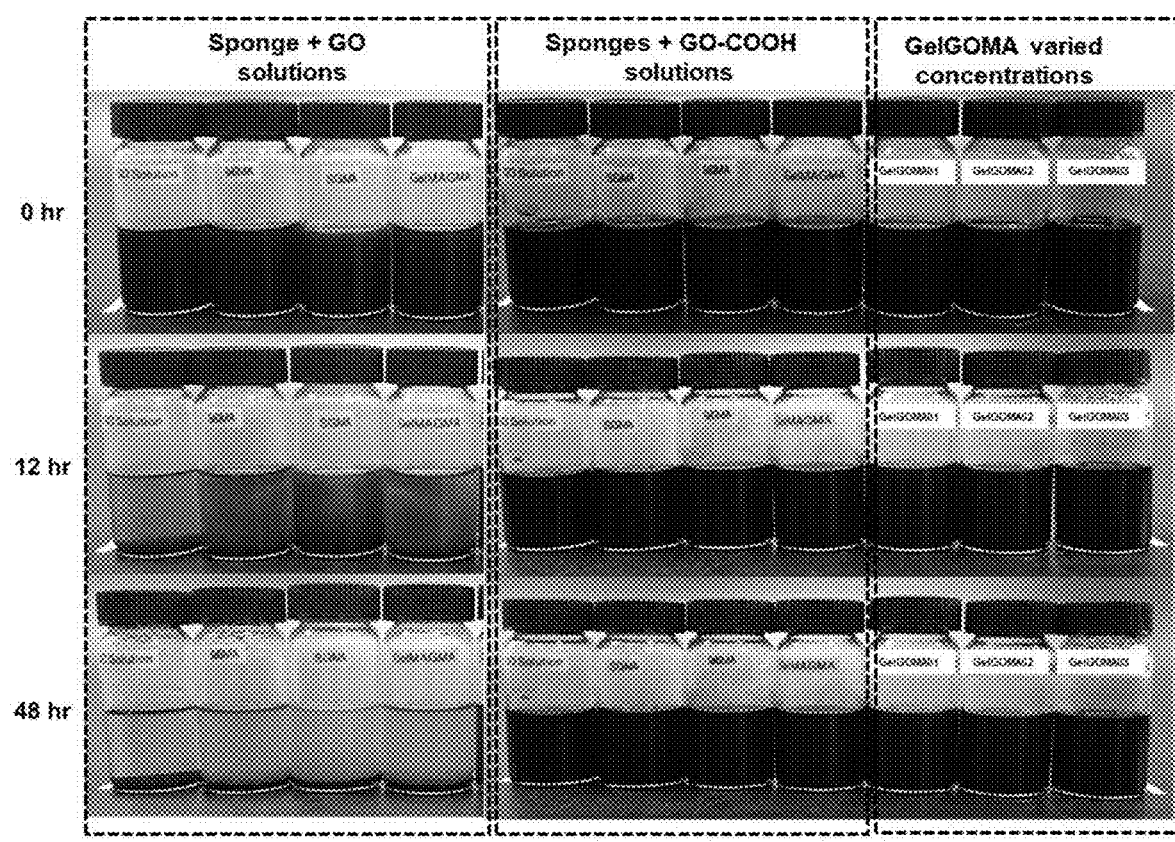
FIG. 3 shows the solubility, dispersion, and sedimentation of GelGOMA solutions. Representative digital images of GelGOMA solutions showing time-dependent dispersion and solubility relatives to the mixture of GO with methacrylated sponges (sponge+GO solutions) and methacrylated sponges with carboxylated GO (sponges+GO-COOH solutions).

Agglutination and precipitation of biocomposite are evidence of poor conjugation. A dispersion test was carried out to confirm the interactions and dispersion behavior of GO-COOH particles in the polymer backbone as shown in FIG. 3. Wherein, 5 mg/mL sponges solution prepared in distilled water (DW) were left standing at room temperature. The images were taken to investigate nanoparticles' sedimentation, dispersion, and distribution in the methacrylated polymer solutions. A few hours of standing displayed the sedimentation and phase separation between the polymer backbone and nanocomposites in physically mixed groups.

Figure 4A:
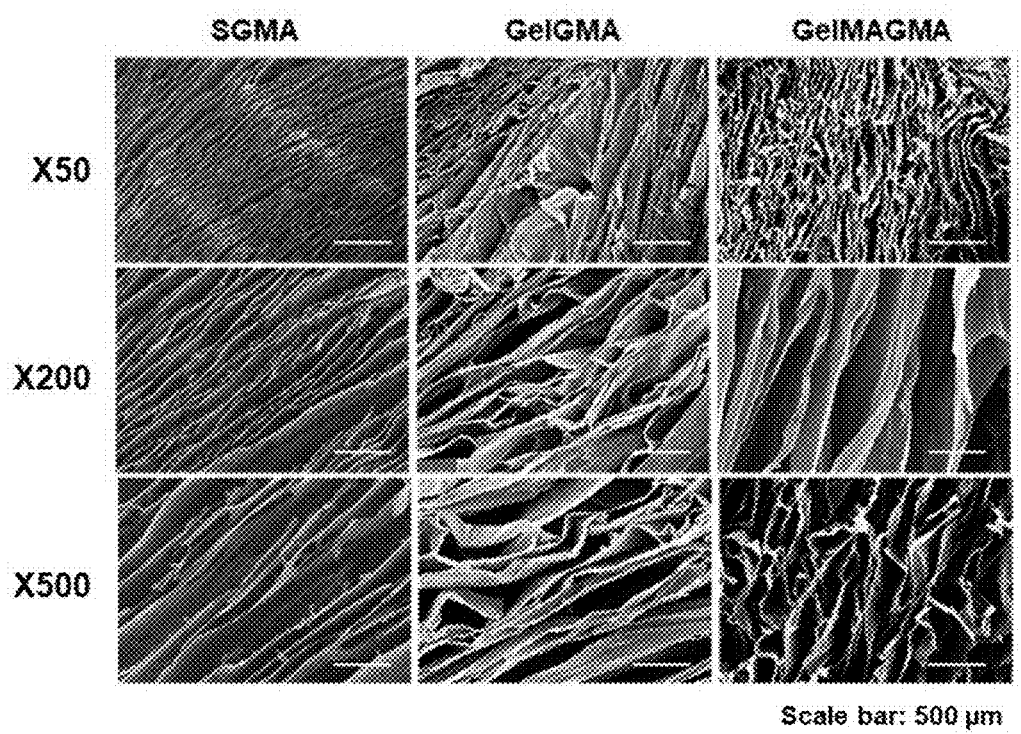
FIG. 4A shows the micrographs of fabricated sponges taken with a scanning electron microscope (SEM)
Figure 4B:
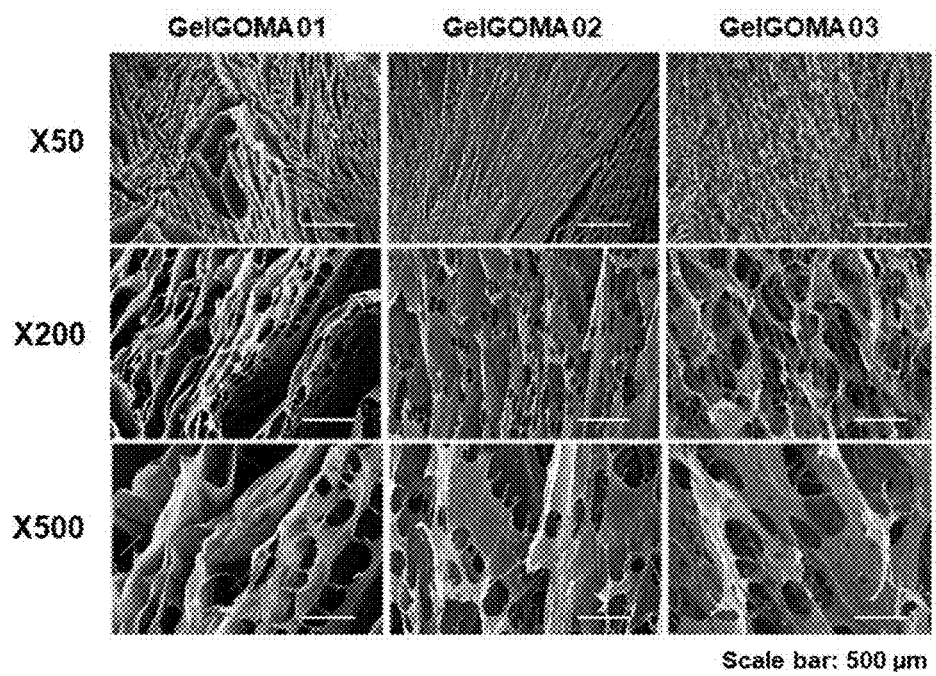
FIG. 4B shows the surface morphology of GelGOMA and incorporation of GO to the methacrylated polymer base via scanning electron microscope (SEM).
Figure 5:
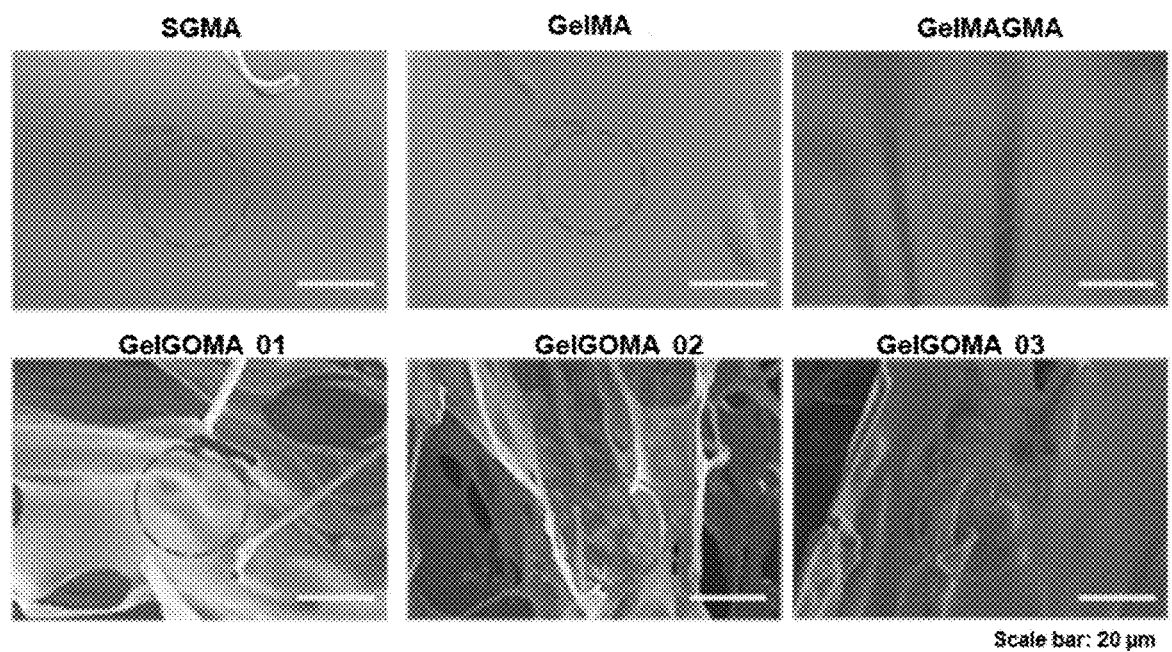
FIG. 5 is an EDX elemental mapping of the fabricated sponge's surface to obtain the C/N/O weight ratio and atomic percent table. The circles indicate the exact points of EDX elemental analyses.

Following FIG. 4, SEM images were able to confirm the porous structure of GelGOMA in which GO was conjugated. The advantage of this is that porous structure can help the proliferation of cells and is one of the factors that increase the physical properties of the hydrogel. Surface compositional analysis through the EDX in Table 1 shows that in some cases, atomic % of carbon has values at most 57.87% and at least 51.07%; oxygen has at least 22.0% and at most 41.21%; Nitrogen values are at most 24.33% and at least 19.99% across all the samples. The oxygen reduction indicated the availability of delocalized electrons for electrical conductivity.

TABLE 1

Table of Carbon/Nitrogen/Oxygen weight ratio and atomic percent

|   | GO | SGMA | GelGMA | GelMAGMA | GelGOMA 01 | GelGOMA 02 | GelGOMA 03 |
|---|---|---|---|---|---|---|---|
| C | 57.87 | 53.28 | 51.07 | 52.07 | 54.79 | 55.81 | 57.83 |
| N | — | 19.99 | 24.33 | 24.33 | 21.35 | 20.96 | 20.08 |
| O | 41.21 | 26.73 | 24.60 | 23.60 | 23.86 | 23.23 | 22.0 |
| Total | 99.08 | 100 | 100 | 100 | 100 | 100 | 100 |

Figure 6A:
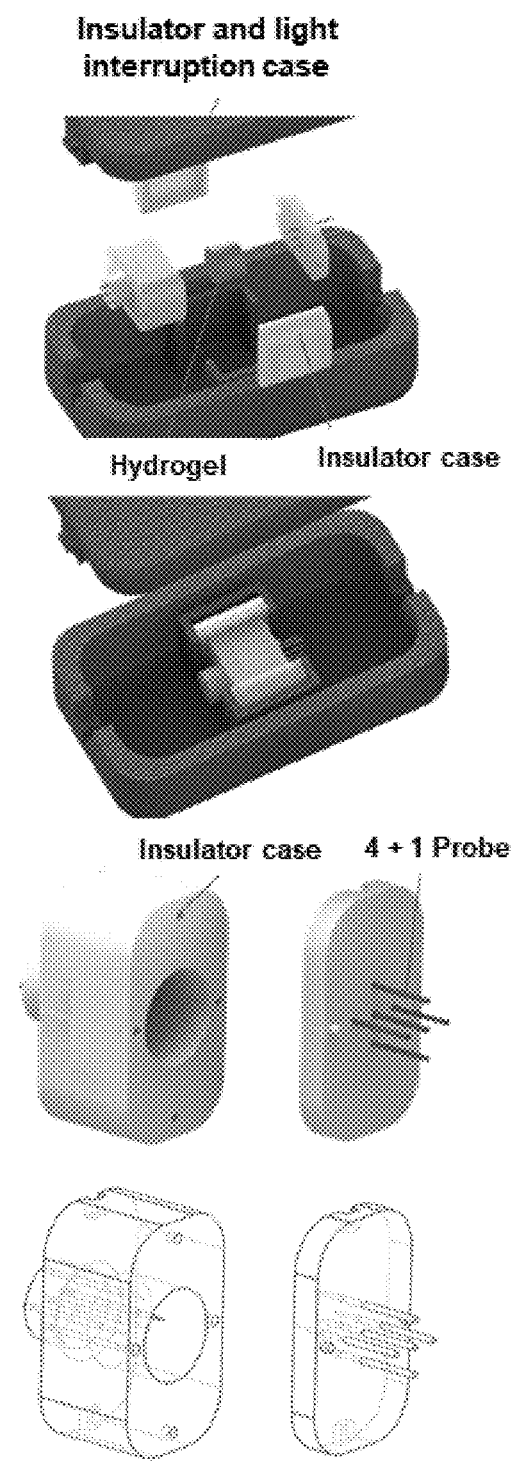
FIG. 6A Four-point probe EIS cell model printed with DLP printer from insulating and photocurable resin.

The present disclosure embodied the electrical conductivity of hydrogel. The removal of oxygen through the conjugation process of GO with GelMAGMA increases its electrical activity by creating unpaired electrons and overlapping orbitals wherein delocalized electrons can freely move through the gel matrix. We confirmed the conductivity by modified electrical impedance spectroscopy (EIS). The 4-probe insulating cell model was made by mounting a total of 10 gold-coated stainless electrodes, 5 on each side, in a 3D-printed insulating mold. Five needle-shaped electrodes on each side of the cell consisted of four outer electrodes providing current and one central electrode measuring voltage (See FIG. 6A).

Figure 6B:
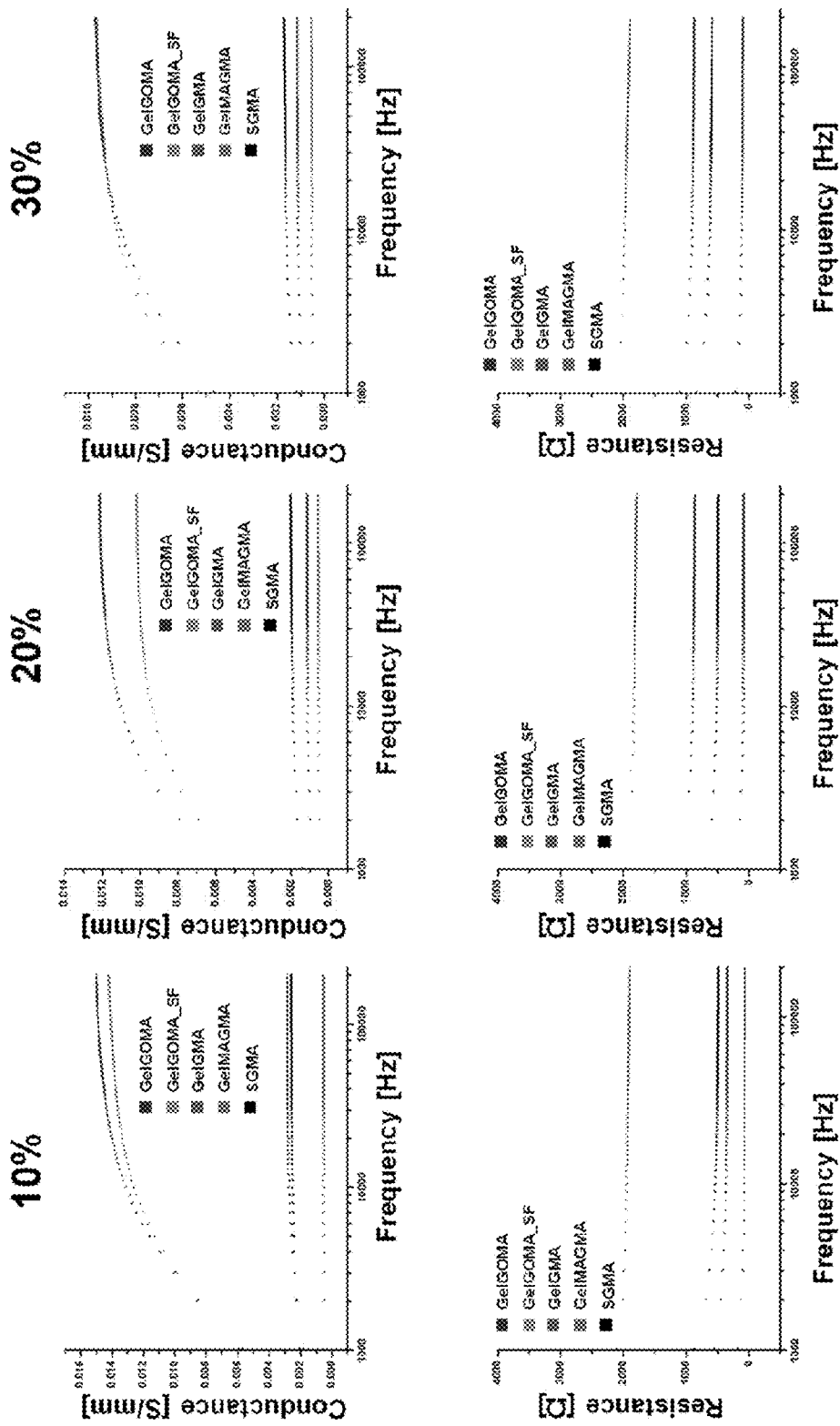
FIG. 6B Graphs of the electrical conductance of GelGOMA and other hydrogels with varying frequencies at different hydrogel concentrations.
Figure 6C:
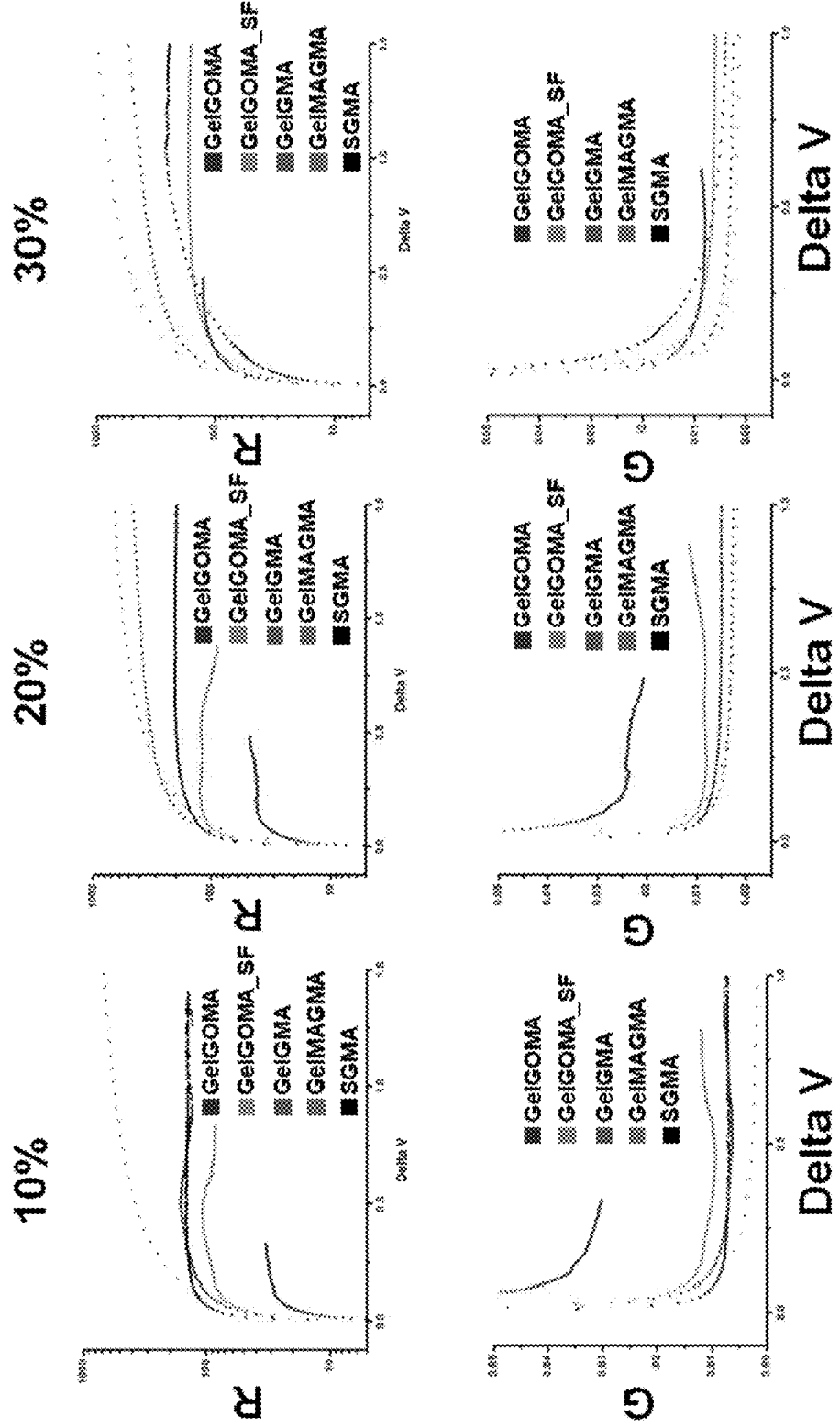
FIG. 6C shows the results of the current-voltage (I-V) curve measurement of hydrogels at different concentrations.
Figure 7A:
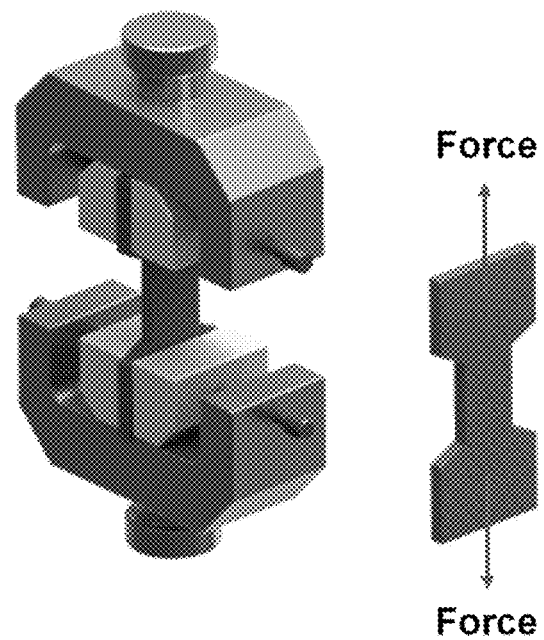
FIG. 7A is a schematic representation of the tensile test experimental setup.
Figure 7A:
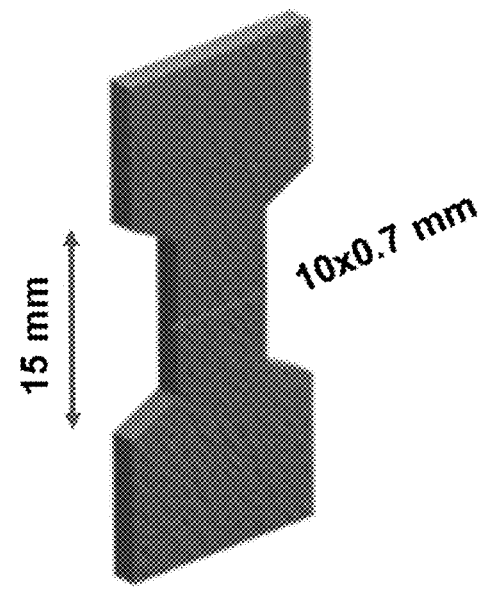
Figure 7B:
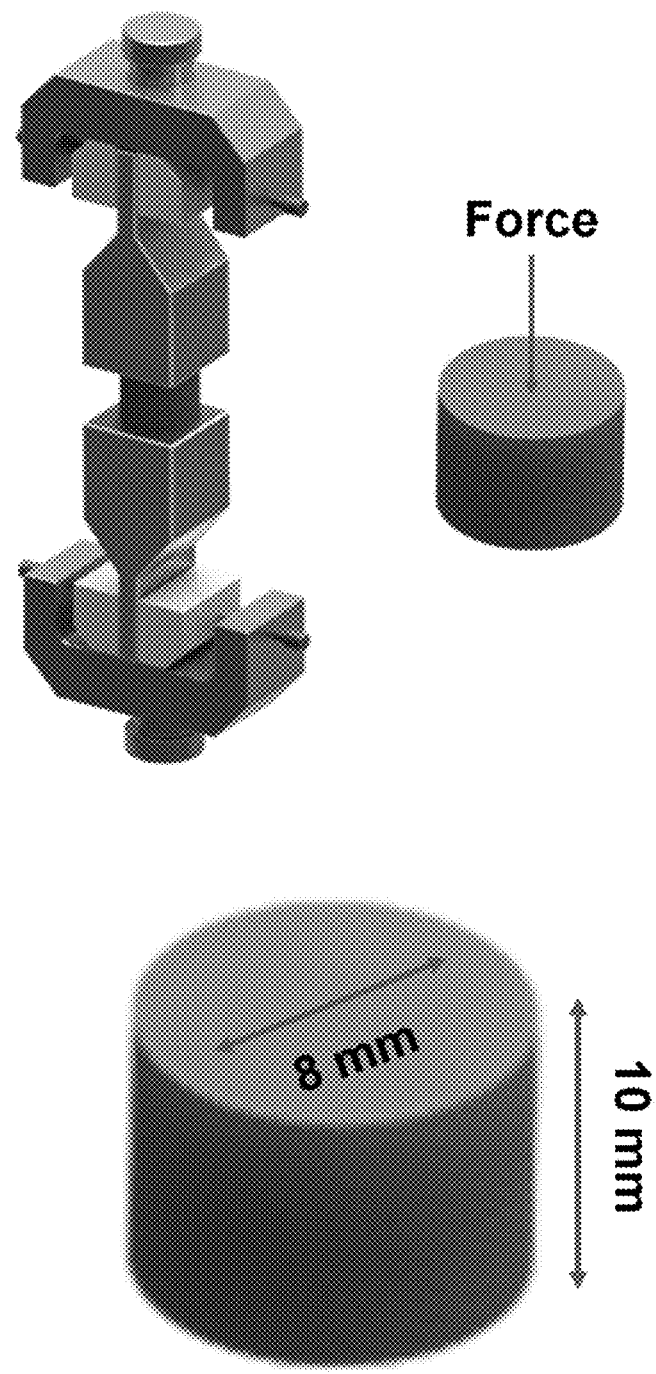
FIG. 7B is a representative model for the compressive test setup.
Figure 7C:
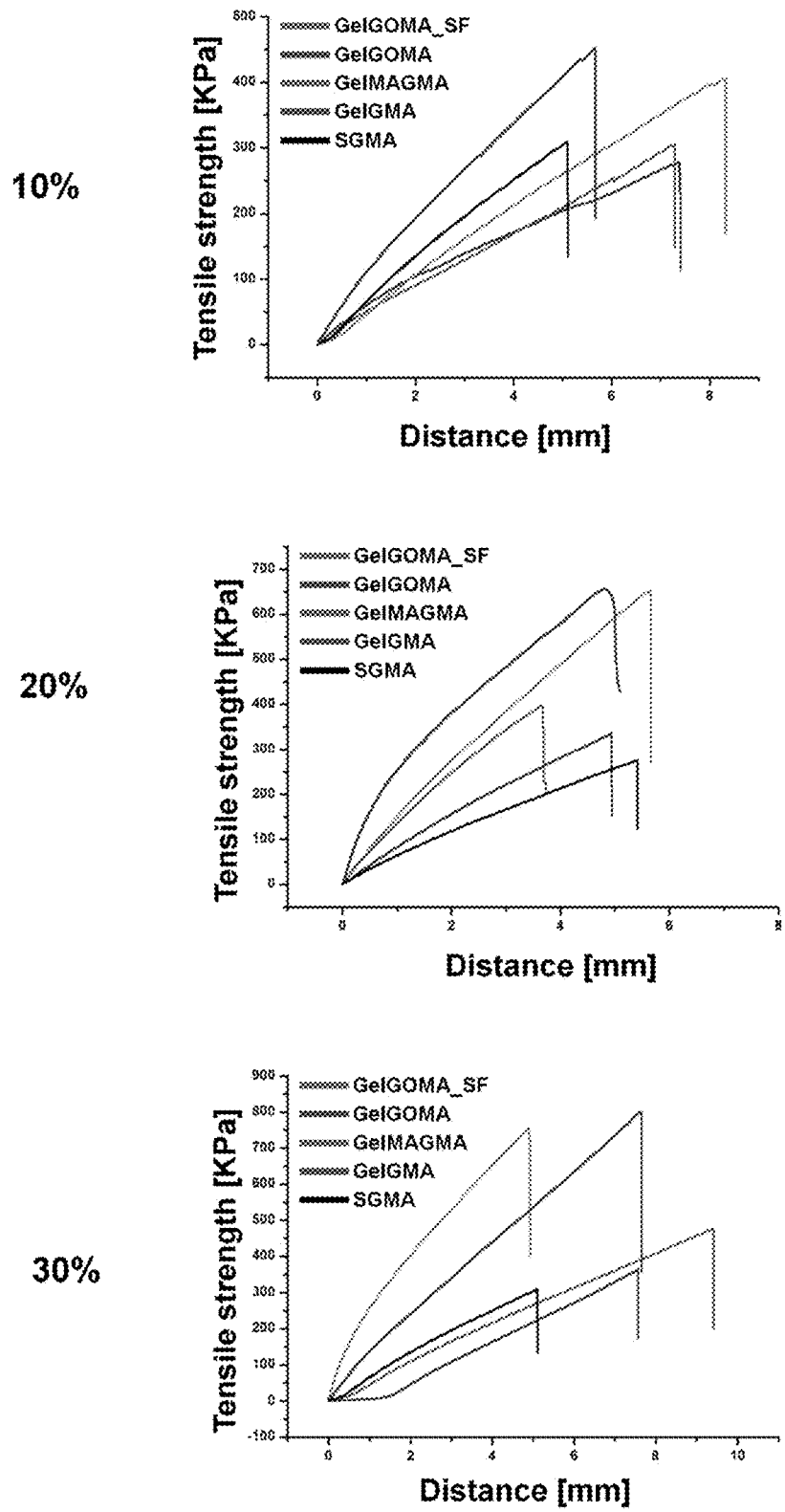
FIG. 7C shows the graphs of tensile stress versus displacement of all fabricated hydrogels at varying concentrations.
Figure 7D:
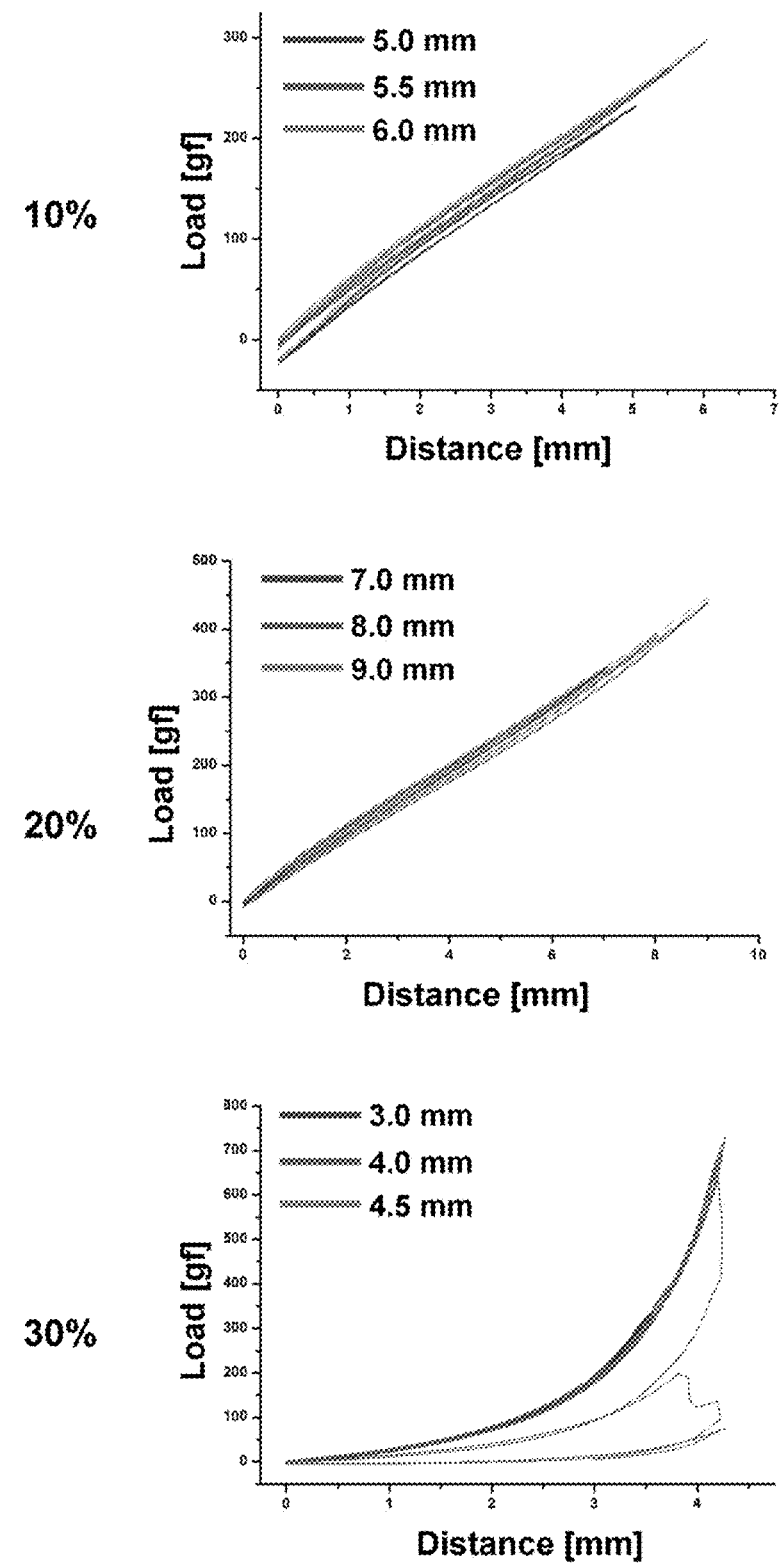
FIG. 7D shows the graphs of cyclic tensile stress of GelGOMA hydrogel across 30% to 90% maximum strain of initial length for the varied concentration of the hydrogels.
Figure 7E:
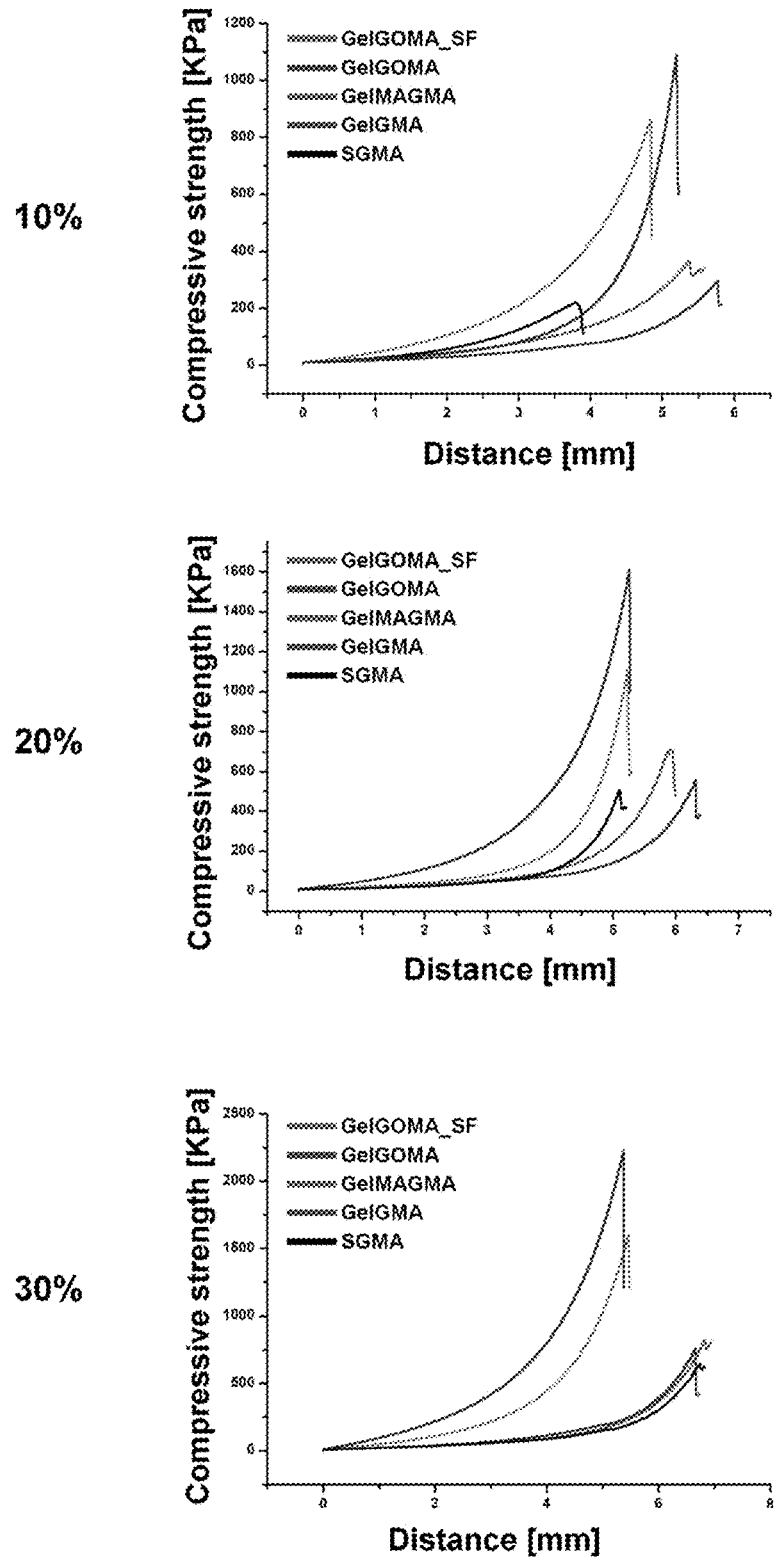
FIG. 7E shows the graph of compressive stress versus displacement of all fabricated hydrogels at different concentrations.
Figure 7F:
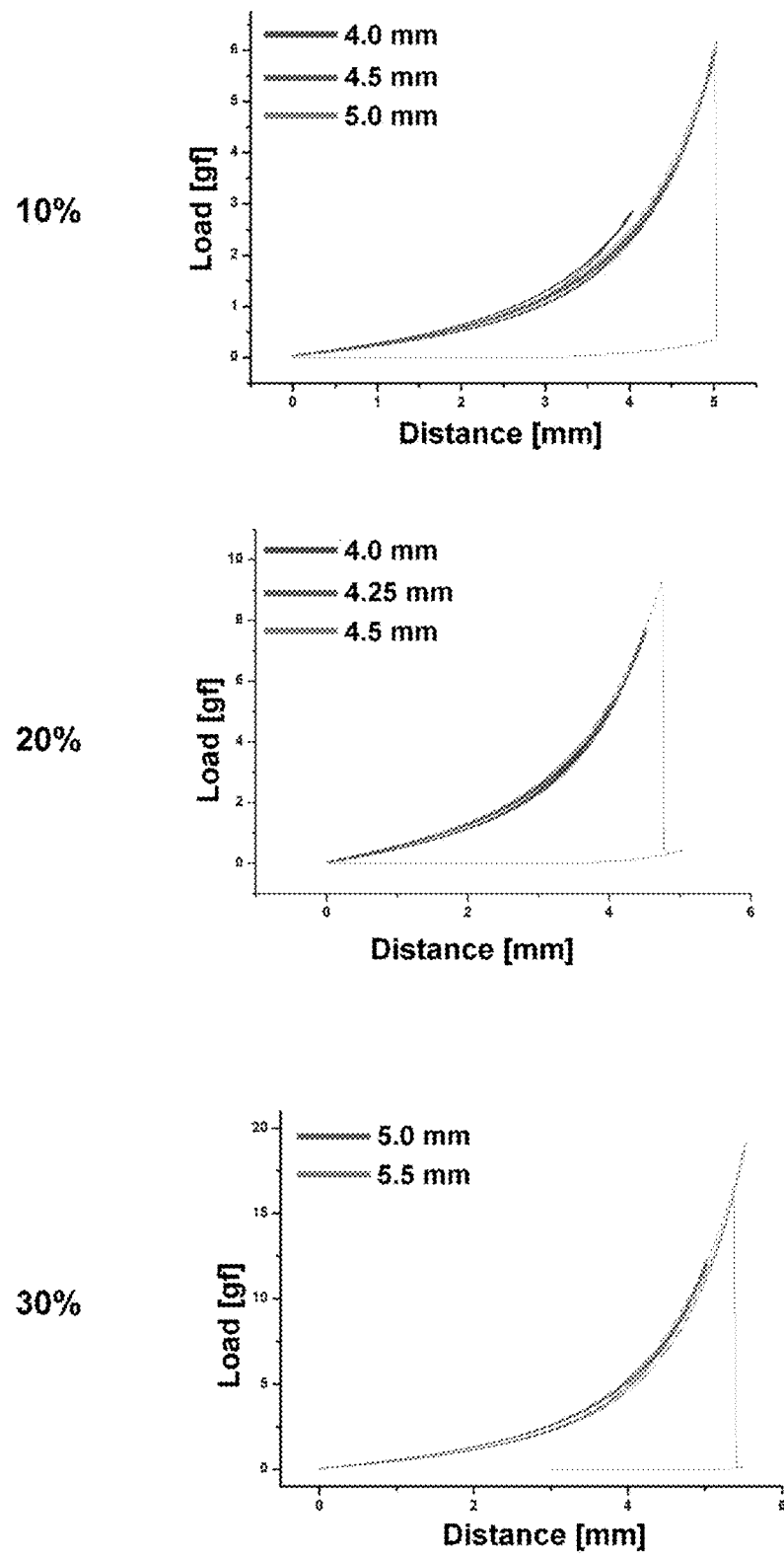
FIG. 7F shows the graphs of cyclic compressive stress of GelGOMA across 40% to 55% maximum displacement of initial height for the varied concentration of the hydrogels.
Figure 8A:
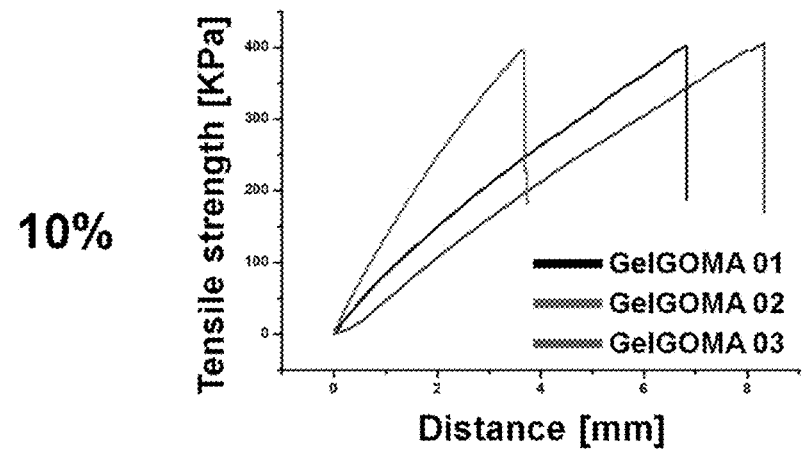
FIG. 8A shows the graphs of tensile strengths of GelGOMA made from 10, 20, or 30% (w/v) bioinks at varied concentrations of GO (i.e., GelGOMA 01, GelGOMA 02, and GelGOMA 03).
Figure 8A:
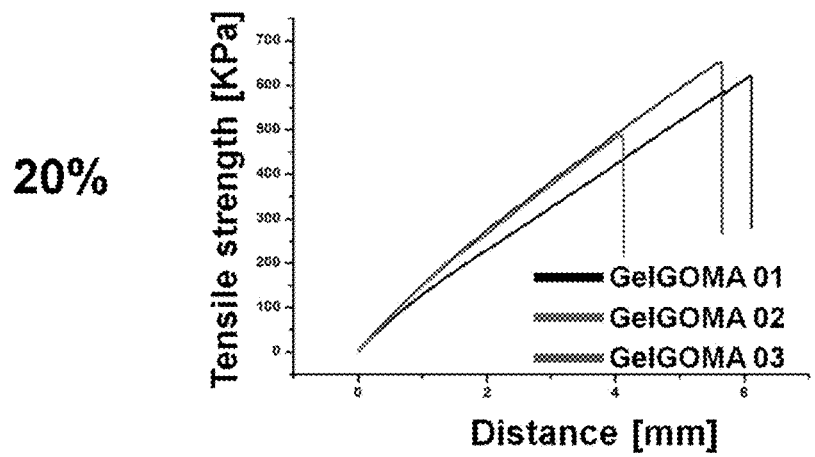
Figure 8A:
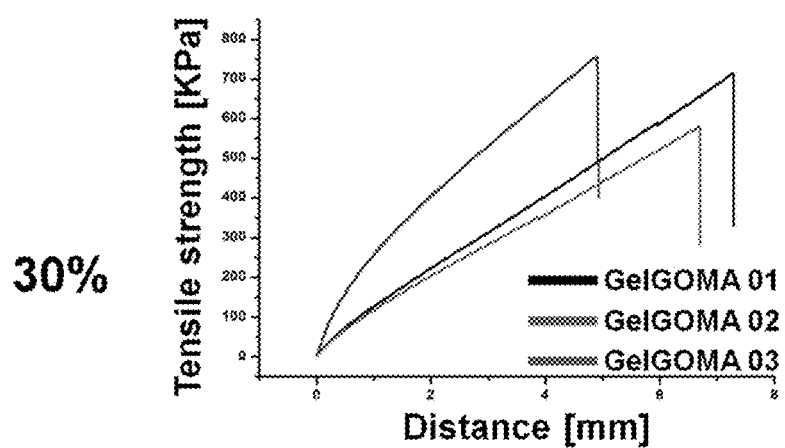
Figure 8B:
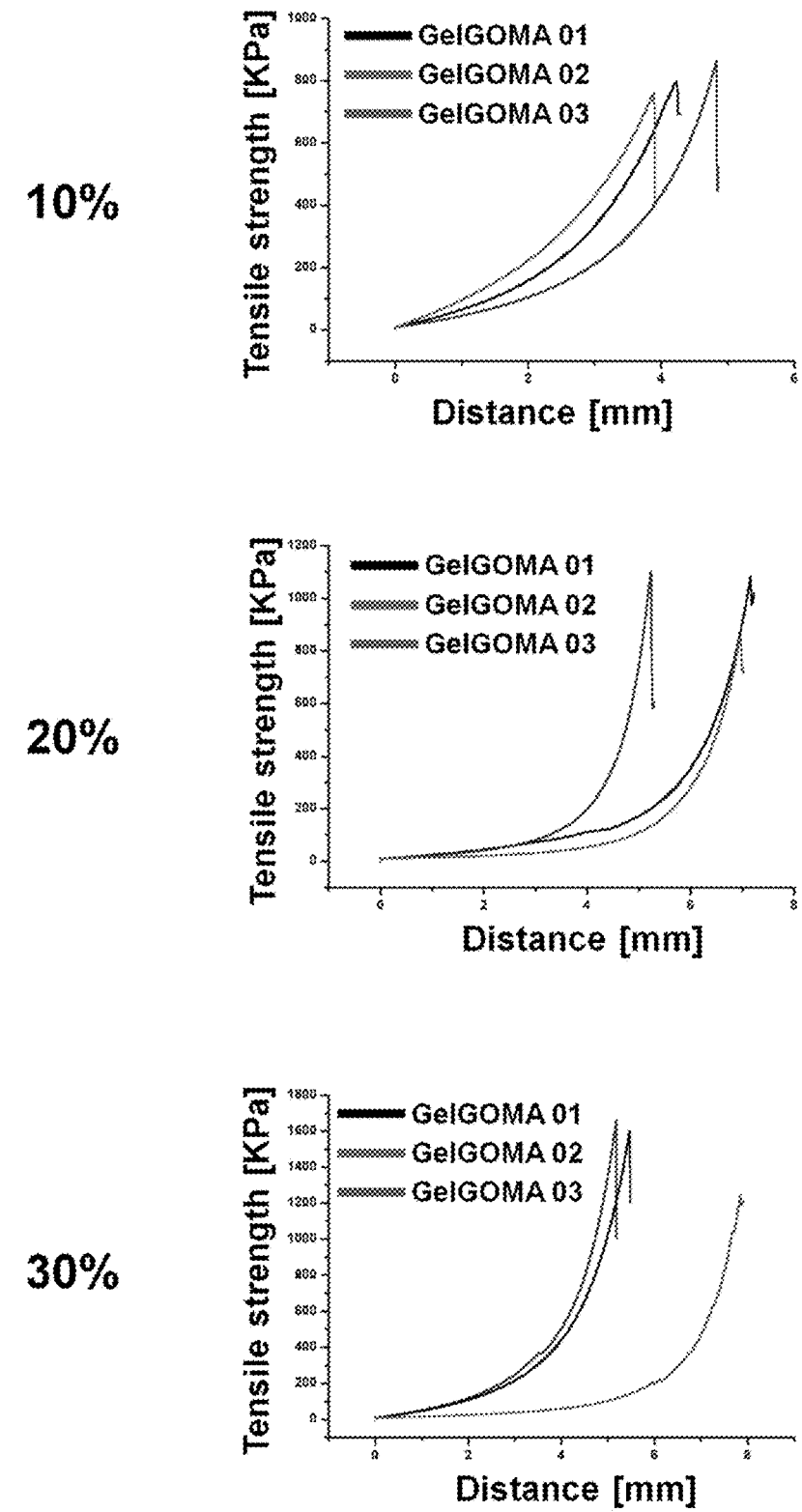
FIG. 8B shows the graphs of compressive strengths of GelGOMA made from 10, 20, or 30% (w/v) bioinks at varied concentrations of GO (i.e., GelGOMA 01, GelGOMA 02, and GelGOMA 03).

Hydrogel conductance measurement was performed using both C-F and I-V methods to increase the reliability. First, in the C-F method, measurements were made in the range of 20 Hz to $2 \times 10^5$ Hz. As a result, all of the measured hydrogels became independent of frequency at some point. In some instances, both GelGOMA and GelGOMA_SF groups showed a difference of up to 100 times in conductivity compared to the least electrically conductive hydrogel without GO (See FIGS. 6B and 6C).

However, it can be seen from Table 2 that the conductivity difference between GO-linked and non-GO-linked hydrogel ranges from 9 to 100 times in some instances. Conversely, the resistance value showed a difference of at least 7 times to a maximum of 400 times as opposed to conductivity in some instances.

TABLE 2

Summary table of comparative electrical conductivities of hydrogels

|  | SGMA (S/mm) | GelGMA (S/mm) | GelMAGMA (S/mm) | GelGOMA 02_SF (S/mm) | GelGOMA 02 (S/mm) |
|---|---|---|---|---|---|
| 10% | $0.0026 \pm 7.1 \times 10^{-6}$ | $0.0029 \pm 9.3 \times 10^{-6}$ | $0.00050 \pm 3.9 \times 10^{-7}$ | $0.0142 \pm 4.4 \times 10^{-5}$ | $0.015 \pm 2.4 \times 10^{-5}$ |
| 20% | $0.0020 \pm 3.2 \times 10^{-6}$ | $0.0016 \pm 8.6 \times 10^{-7}$ | $0.0006 \pm 1.8 \times 10^{-5}$ | $0.0101 \pm 7.4 \times 10^{-5}$ | $0.0121 \pm 1.7 \times 10^{-5}$ |
| 30% | $0.0017 \pm 8.7 \times 10^{-6}$ | $0.0011 \pm 7.0 \times 10^{-8}$ | $0.0005 \pm 1.2 \times 10^{-5}$ | $0.0097 \pm 1.4 \times 10^{-5}$ | $0.0097 \pm 4.2 \times 10^{-5}$ | kPa. The cyclic test affirmed that in some instances, hydrogels regain their initial structures after 55 and 90% stretching or compression for 10 consecutive times except at a high concentration of 30% (w/v).

Both tensile strength and compressive strength results from tables 3 and 4 showed that the strength increased as the concentration of GO increased, but the physical properties decreased when more than a certain amount of GO was added.

TABLE 3

Summary table of tensile strength of GelGOMA at various concentrations

| KPa | GelGOMA 01 | GelGOMA 02 | GelGOMA 03 |
|---|---|---|---|
| 10% | 402.49 ± 16.3 | 406.42 ± 9.7 | 396.75 ± 12.5 |
| 20% | 621.6 ± 12.9 | 652.28 ± 13.8 | 489.63 ± 18.4 |
| 30% | 715.75 ± 20.5 | 755.67 ± 23.1 | 580.41 ± 27.2 |

TABLE 4

Summary table of compressive strength of GelGOMA at various concentrations

| KPa | GelGOMA 01 | GelGOMA 02 | GelGOMA 03 |
|---|---|---|---|
| 10% | 796.979 ± 26.8 | 863.313 ± 10.8 | 760.886 ± 19.1 |
| 20% | 1079 ± 31.5 | 1103.285 ± 50.3 | 850.632 ± 47.4 |
| 30% | 1661 ± 13.7 | 1602.738 ± 19.3 | 1243.756 ± 23.2 |

Figure 9A:
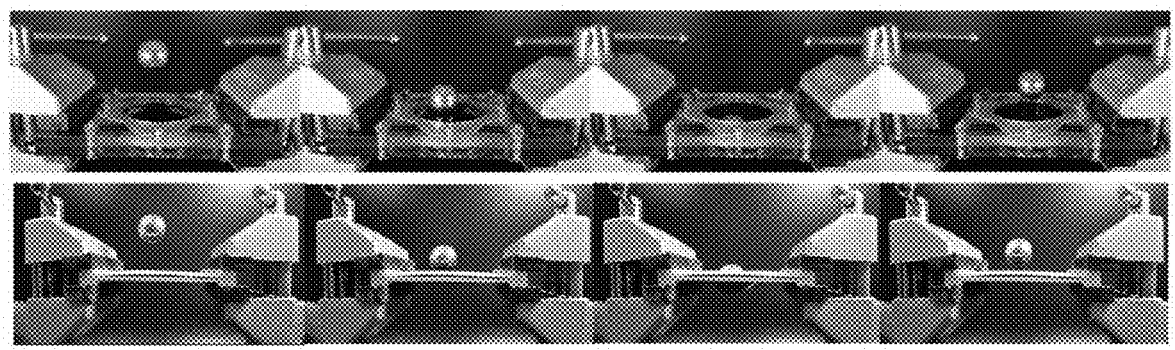
FIG. 9A are representative digital images demonstrating the flexibility, stretchability, and toughness of 20% (w/v) GelGOMA 02 hydrogel to a dropped 500 g iron bead.
Figure 9B:
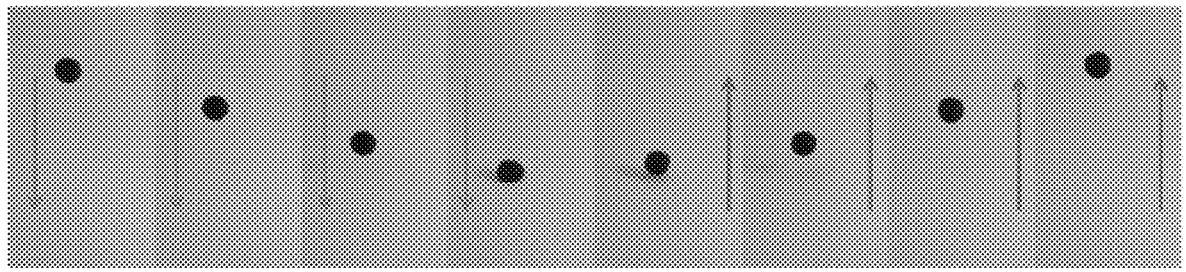
FIG. 9B are digital images of elastic rebound of 20% (w/v) GelGOMA 02 hydrogel bead on a smooth surface.

The major claim of this disclosure is the stretchability and strength of the hydrogel. Through the compressive, tensile, and cyclic tests the mechanical strength of the fabricated structures was affirmed. For both the compressive and tensile strengths, the stress and strain at the breaking point were taken as maximum strength (See FIGS. 7-9).

At least, the tensile strength can be 277.95, 308.91, 406.42, and 454.33 kPa. In some instances, the tensile strength can be at most 364.39 kPa, 476.6 kPa, 755.67 kPa, and 846.87 kPa. The compressive stress in some instances can be at most 756.984 kPa, 822.342 kPa, 1602.738 kPa, and 2226.076 kPa. In some instances, compressive stress can be at least 296.55 kPa, 363.86 kPa, 863.313 kPa, and 1090.603

Figure 10:
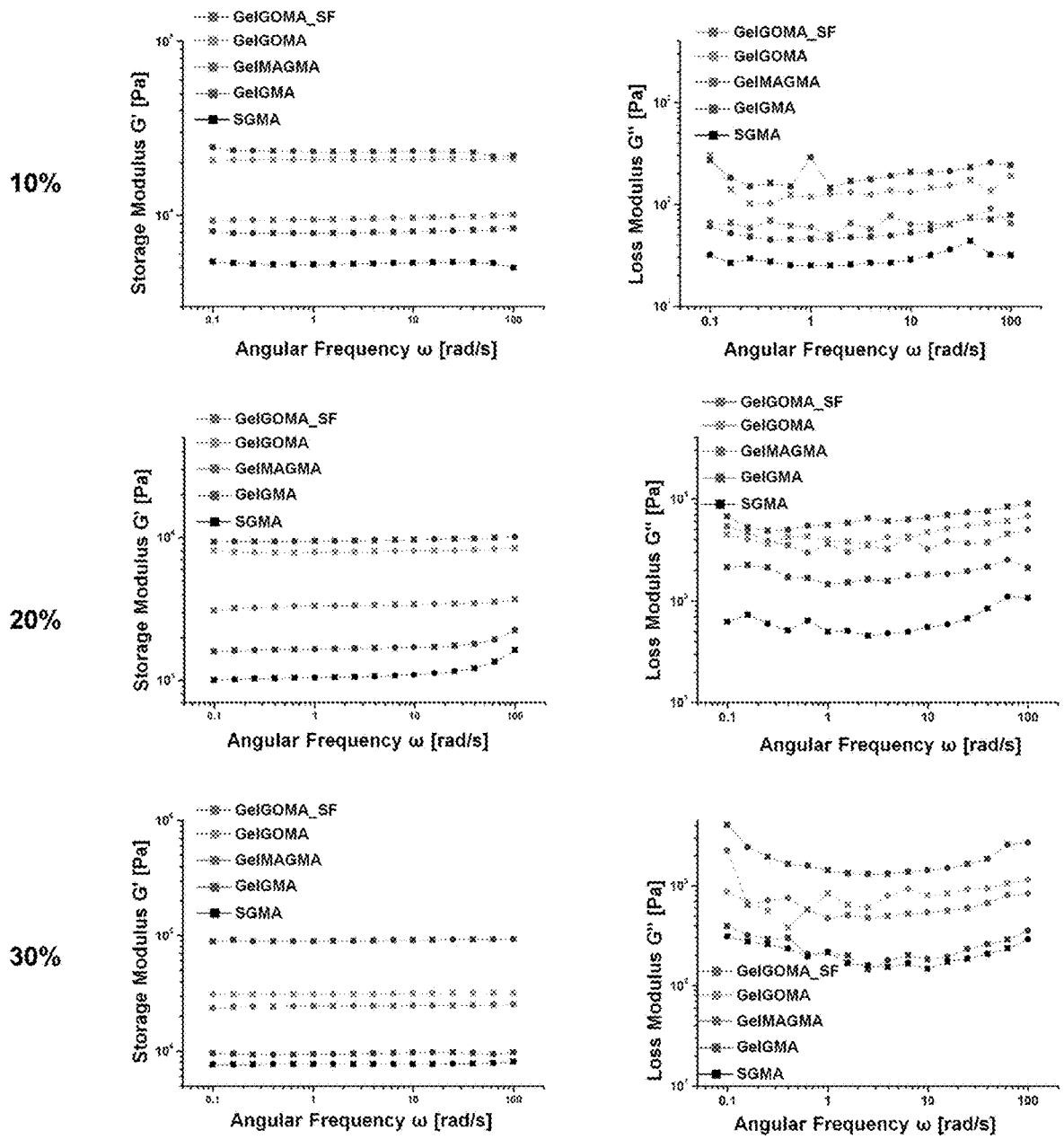
FIG. 10 is the viscoelastic characterization of fabricated hydrogels.
Figure 11:
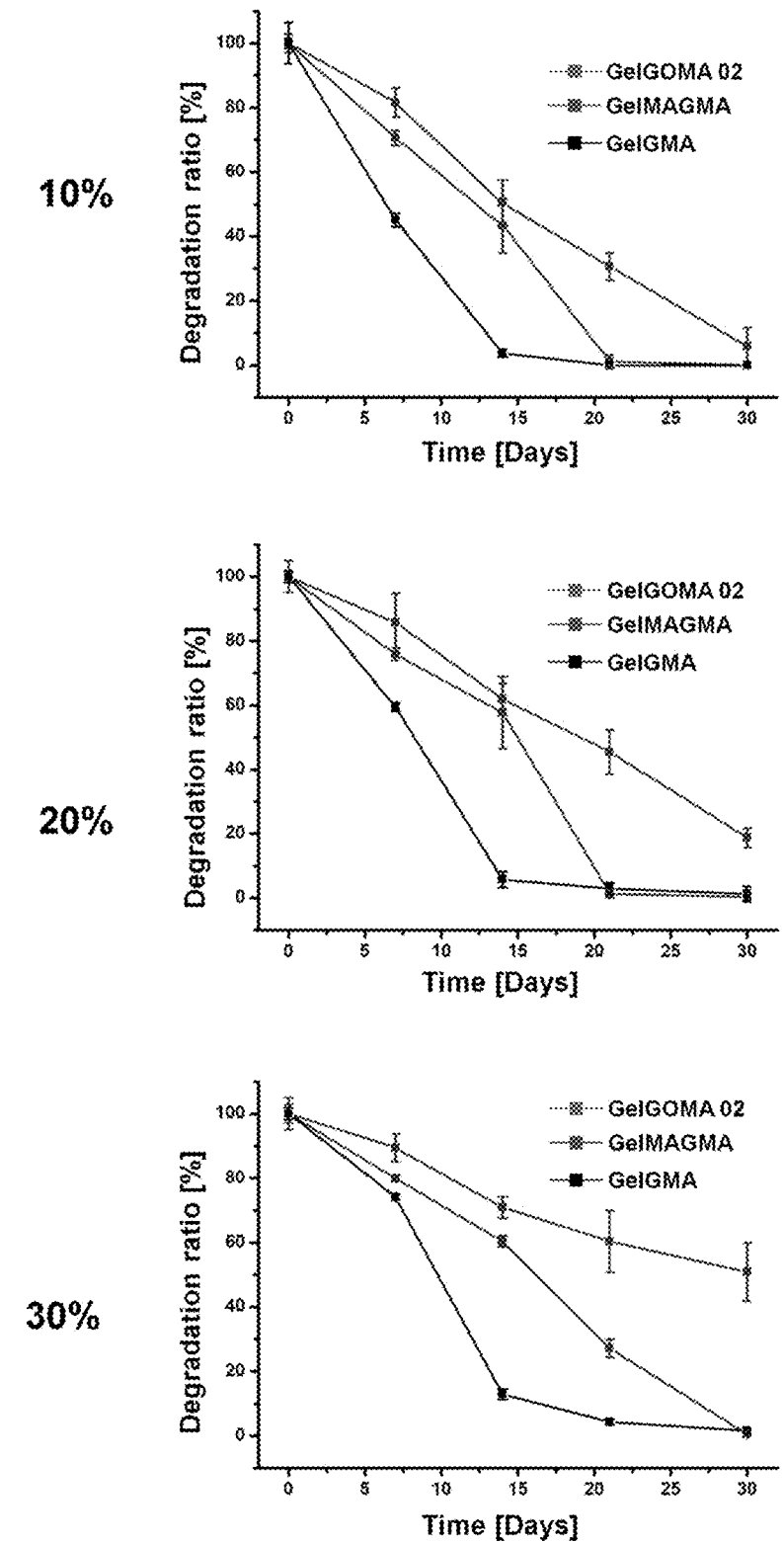
FIG. 11 is enzymatic degradation of 10, 20, and 30% (w/v) GelGOMA 02 hydrogels relative to equivalent concentrations of GelGMA and GelMAGMA hydrogels.
Figure 12A:
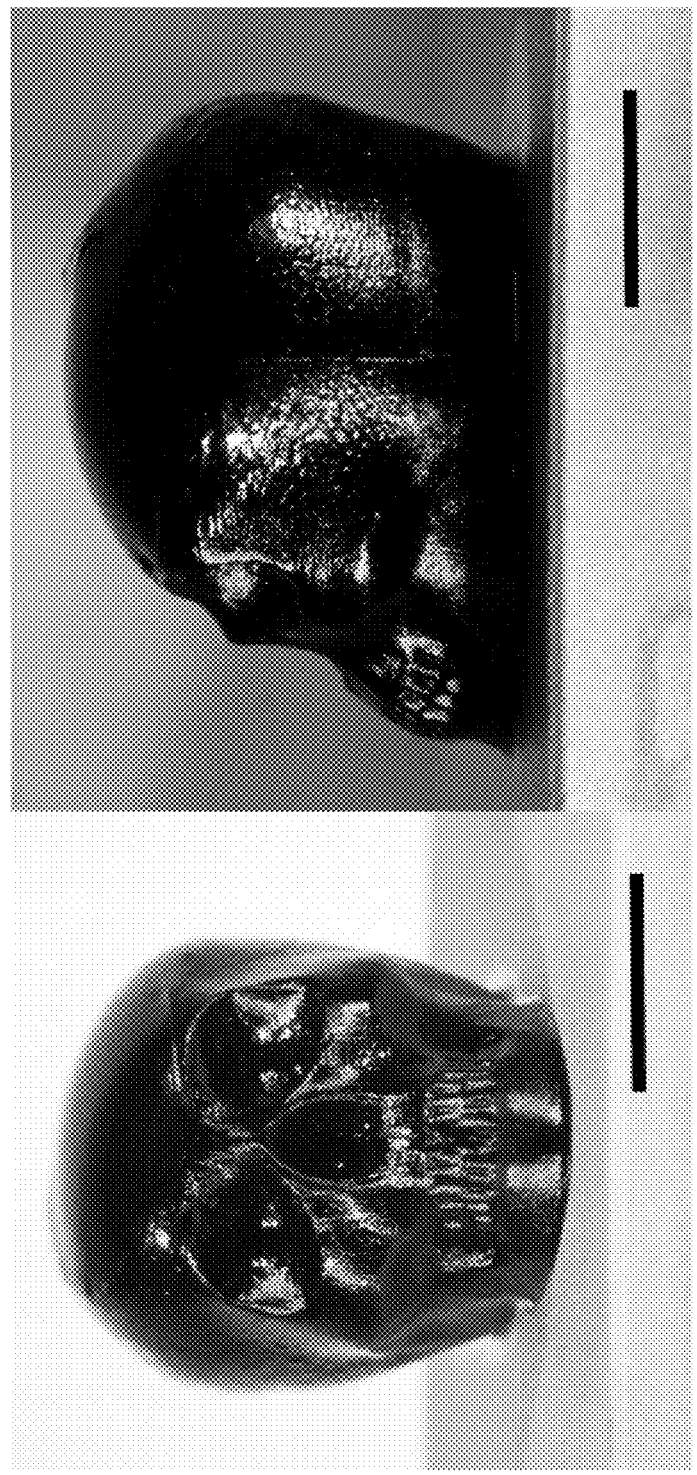
FIG. 12A shows digital images of miniature human skull hydrogel of GelGOMA 02
Figure 12B:
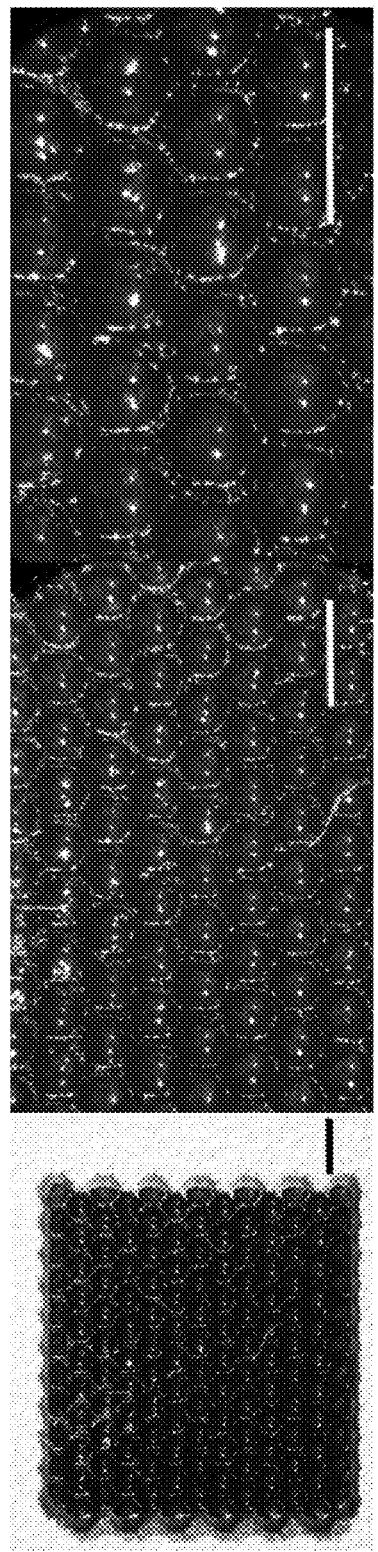
FIG. 12B shows digital images of a cube hydrogel of GelGOMA 02 with 50 μm pores.
Figure 12C:
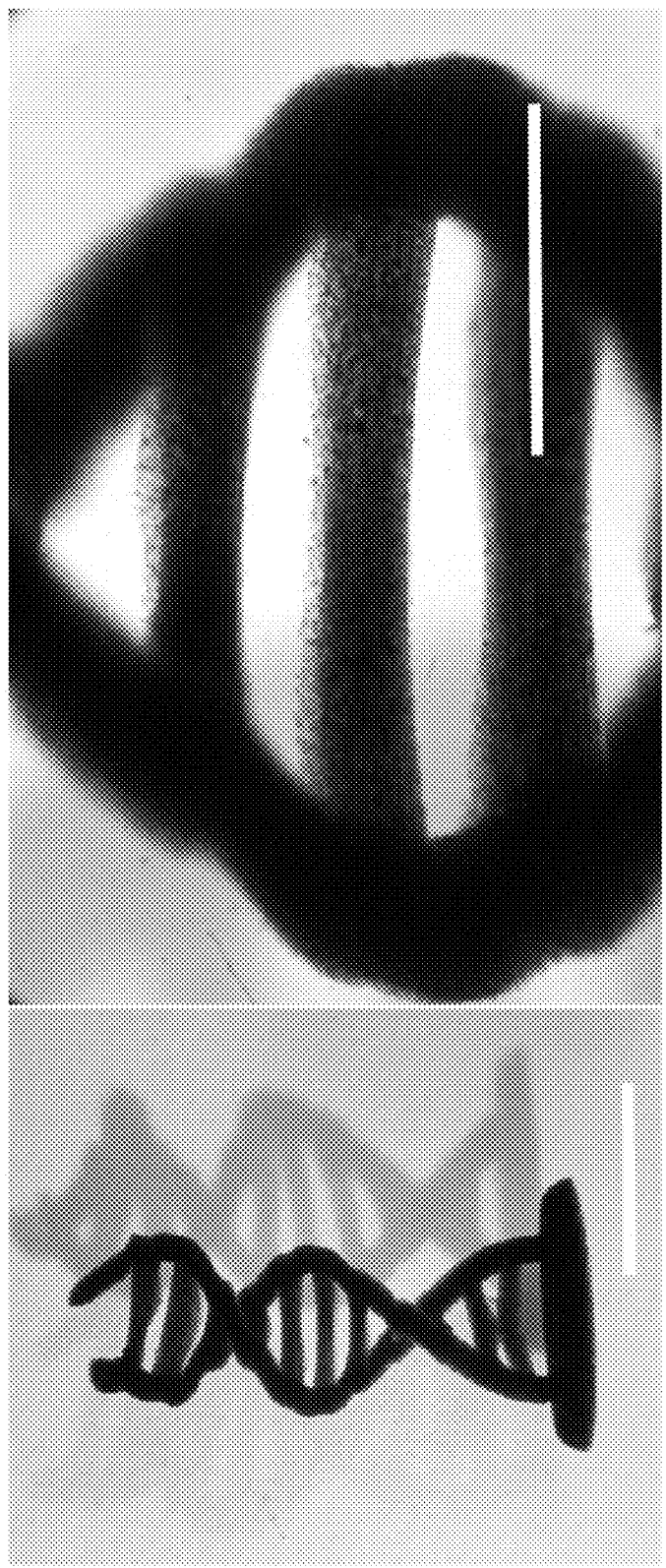
FIG. 12C shows digital images of the DNA double helix hydrogel made from GelGOMA 02.
Figure 12D:
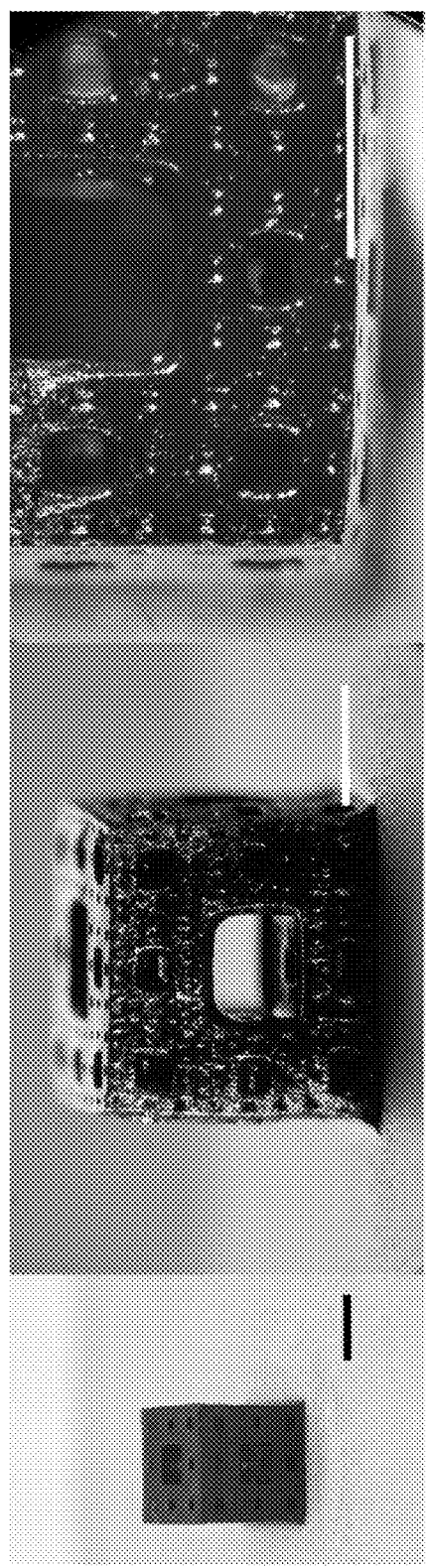
FIG. 12D shows digital images of a porous scaffold (50 μm pore size) made of GelGOMA 02.
Figure 12E:
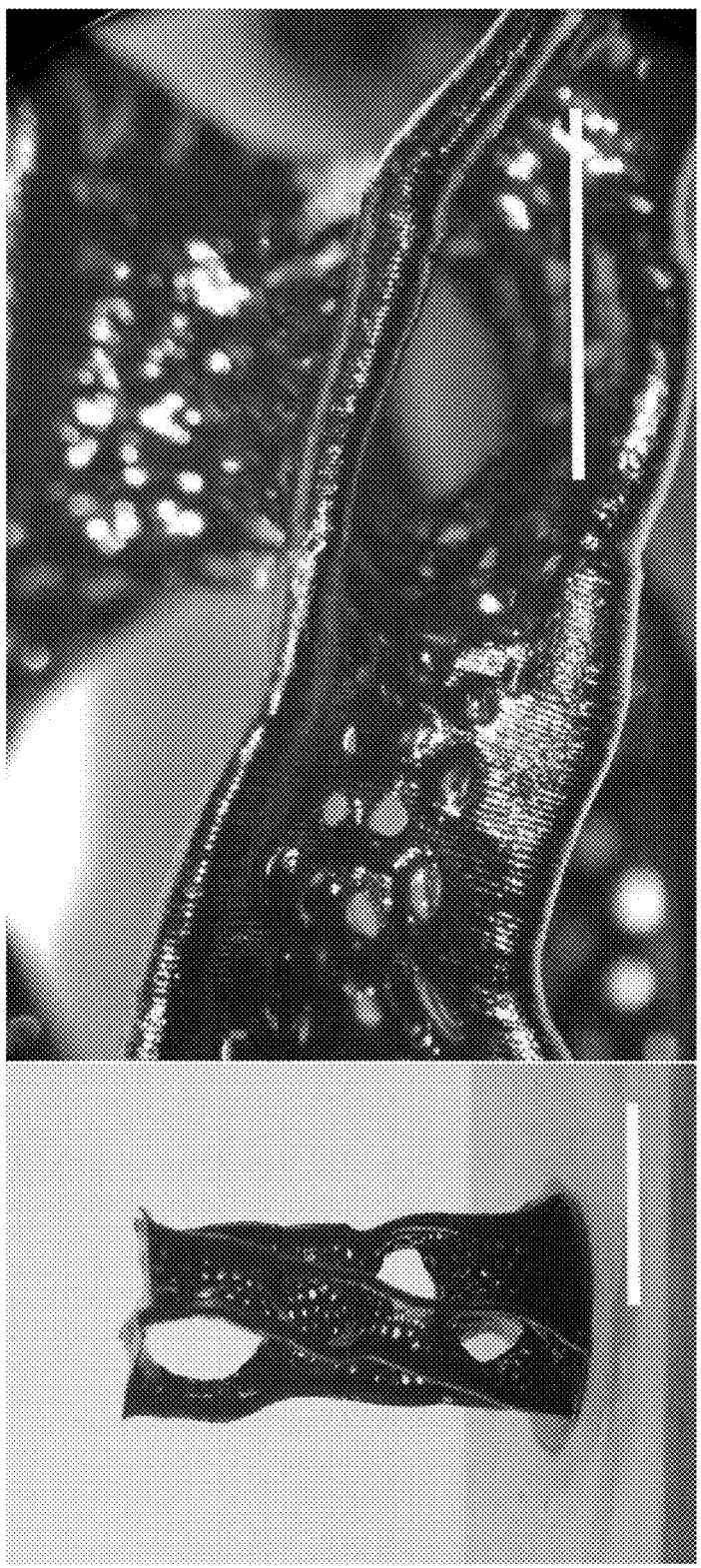
FIG. 12E shows digital images of a geometric structure with <100 μm pore size printed from GelGOMA 02
Figure 12F:
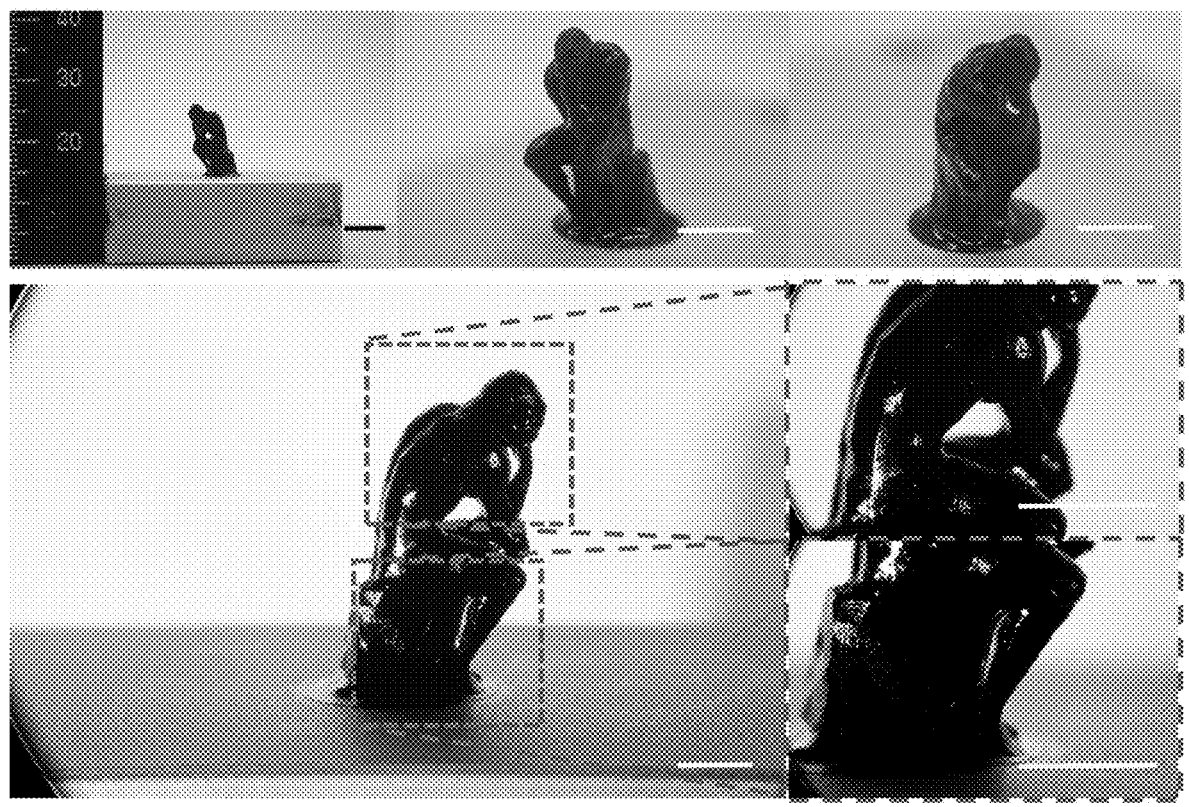
FIG. 12F shows the thinker of Auguste Rodin replica printed from GelGOMA
Figure 12G:
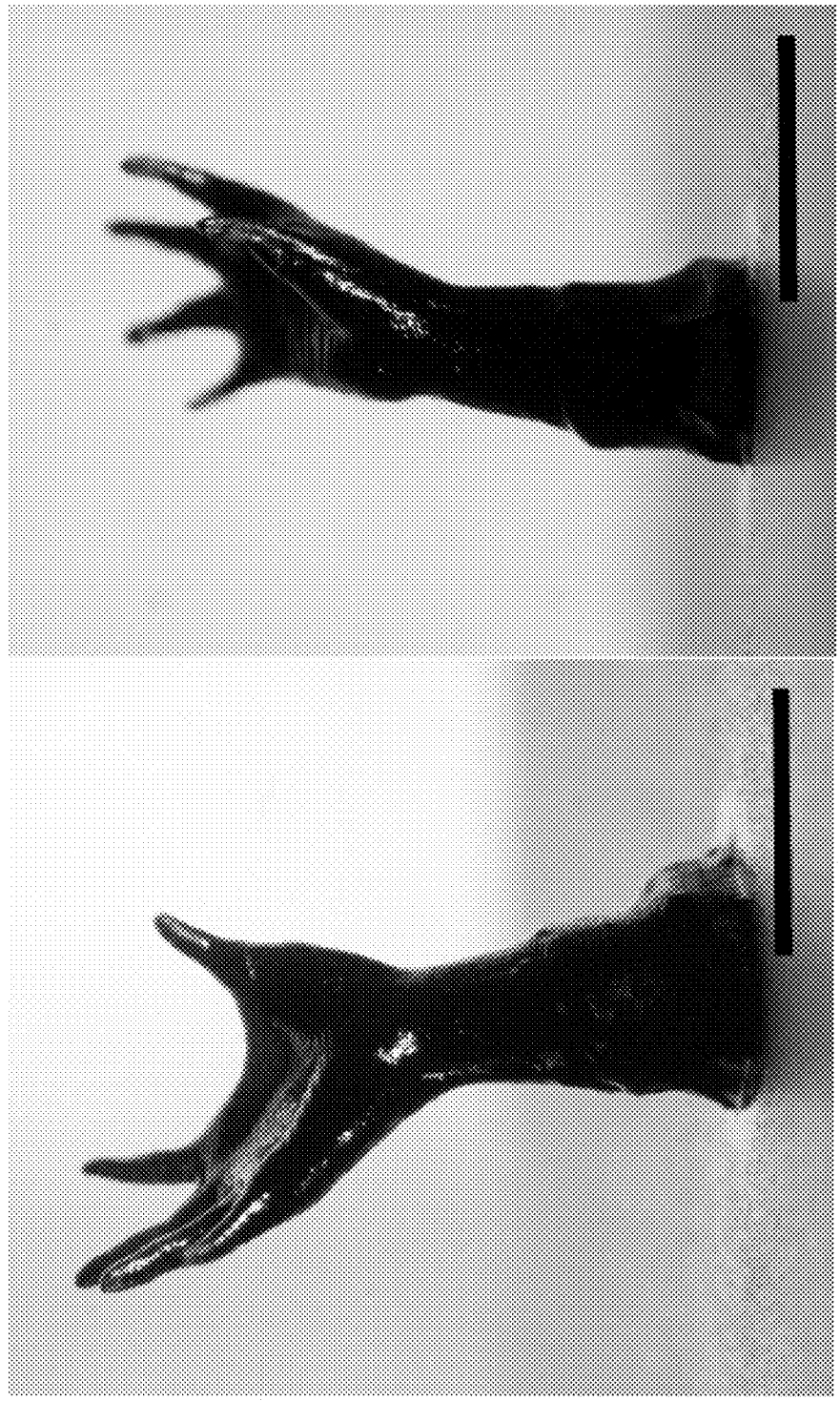
FIG. 12G shows hydrogel images of the micro human hand from GelGOMA 02
Figure 12H:
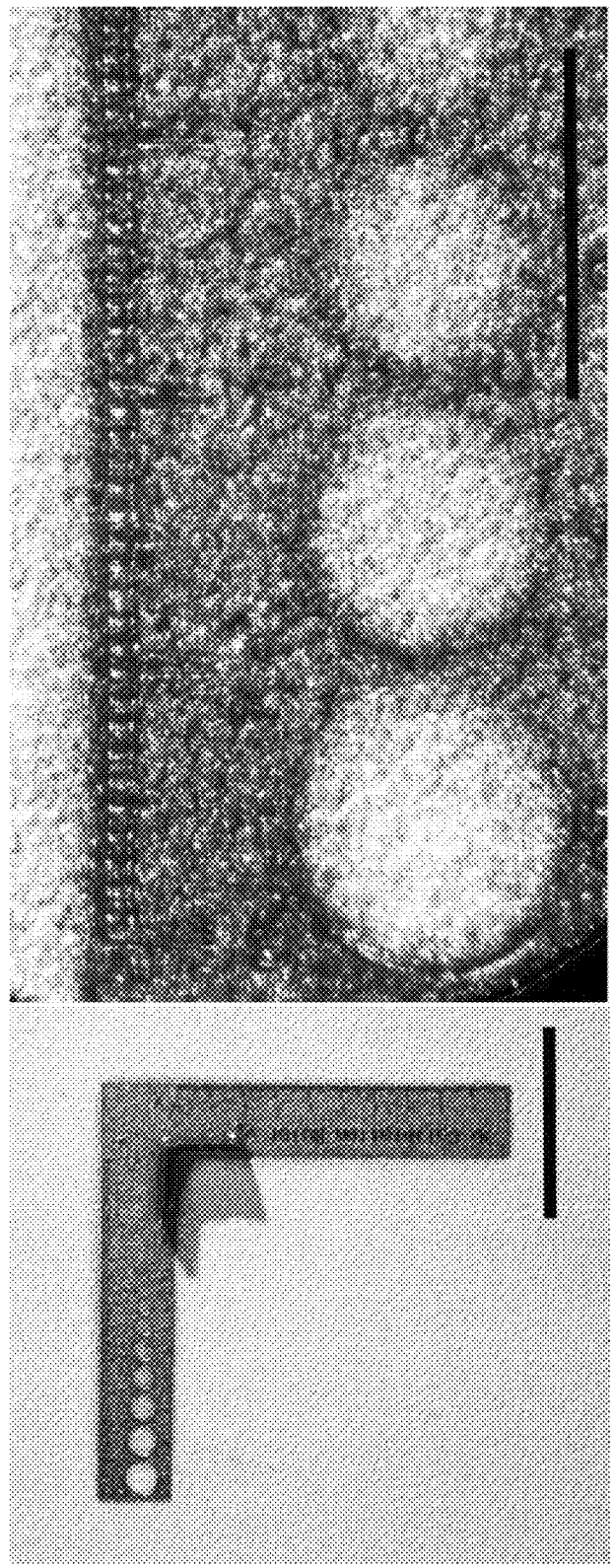
FIG. 12H shows digital images of measuring ruler hydrogel from GelGOMA 02

In all groups, the storage modulus (G') was larger than the loss modulus (G"). This means that all groups of hydrogels exhibited the behavior of elastomeric materials. The ultra-strong hydrogels have impressive storage modulus that signifies the degree of crosslinking within the range of 100 kPa. The constructs demonstrated biodegradability and robust stretchability without compromising structural integrity (See FIGS. 10 and 11).

All structures fabricated using GelGOMA bio-ink were printed with high accuracy in CAD-designed shapes (See FIG. 12). For example, in the human skull-shaped structure, the curves of bones and the shape of fine teeth were realized, and the DNA double helix structure was able to realize a transverse structure with a hole of 100 μm or less without a supporter. In addition, pores with a diameter of 30-100 μm existing in various directions in an irregular structure were printed, and a structure corresponding to the finger part in the shape of a human hand could be realized with a thickness of 20~30 μm. Furthermore, regular pore structure, the flexion, and joint expression of the back muscles in the shape of a human hand smaller than 1 cm were perfectly expressed. We discovered in this disclosure that the detailed micropores on all fabricated structures are achievable without the use of a photoinitiator due to the presence of chemically linked GO.

Figure 15A:
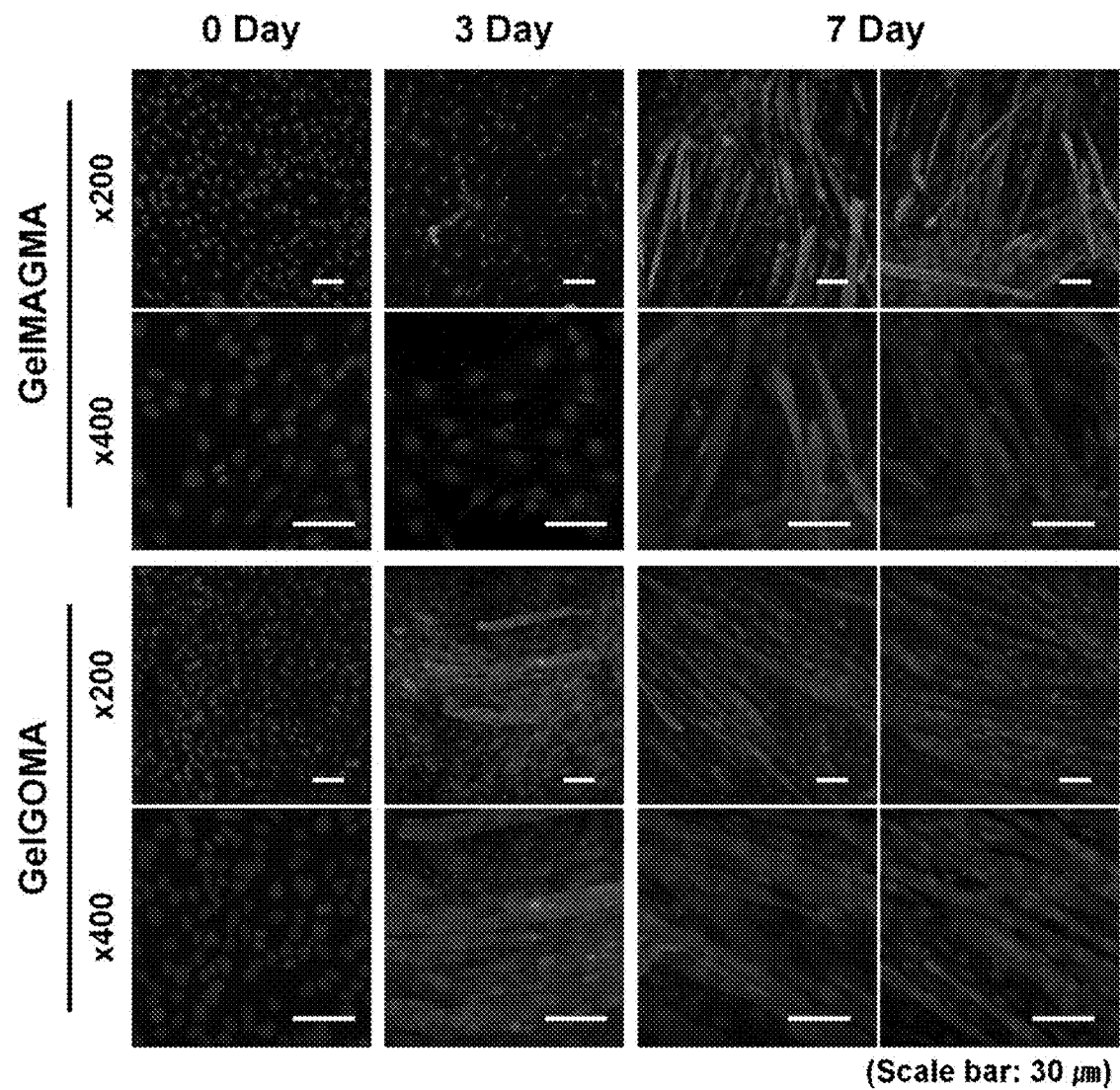
FIG. 15A shows the myosin heavy chain (MHC) immunofluorescence staining for the observation of C2C12 differentiation as evidence of differentiation of electrosensitive cells in GelGOMA hydrogel
Figure 15B:
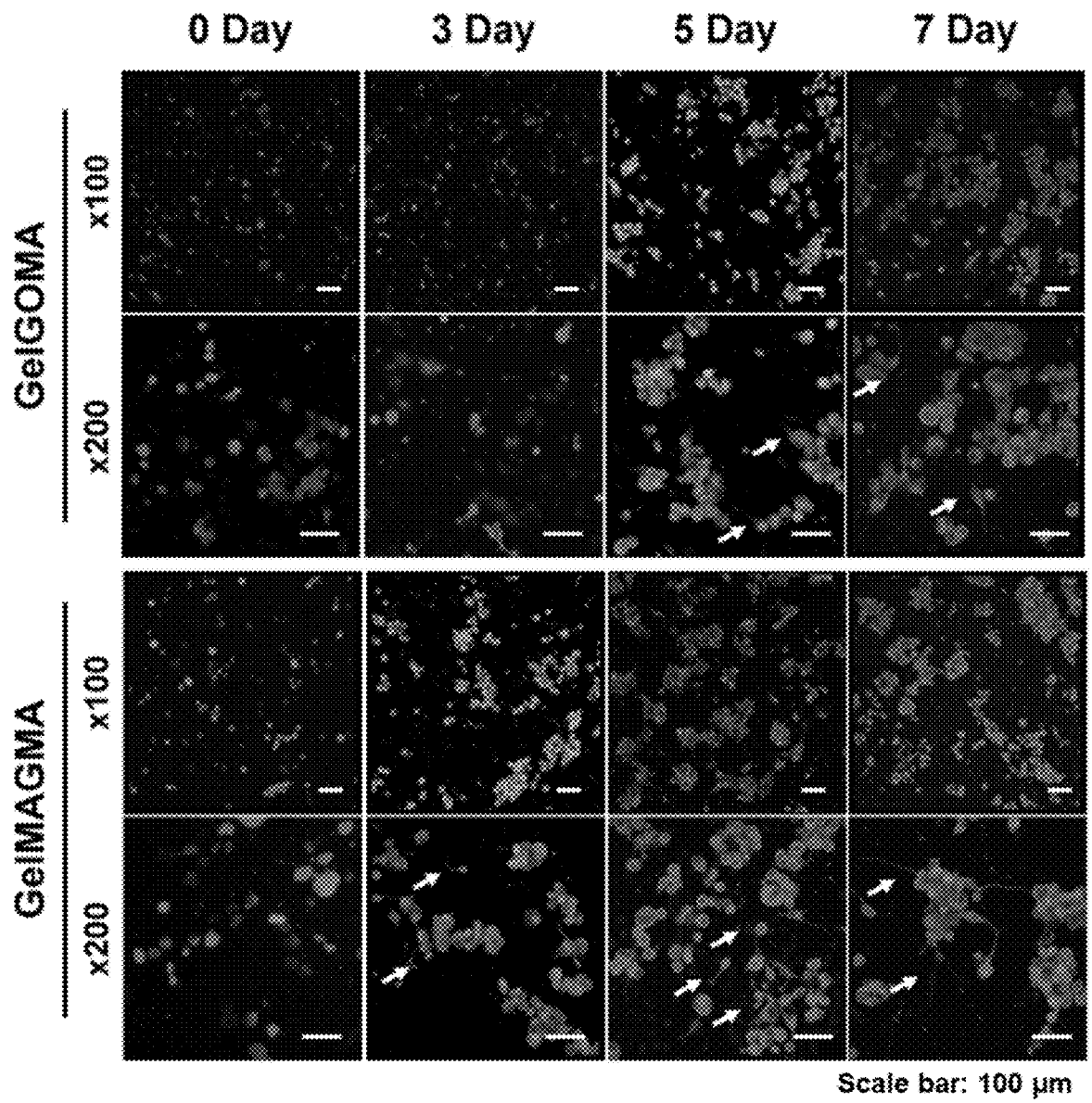
FIG. 15B is alpha-tubulin immunofluorescence staining of Neuro2a to show its neuronal differentiation as evidence of differentiation of electrosensitive cells in GelGOMA hydrogel
Figure 15C:
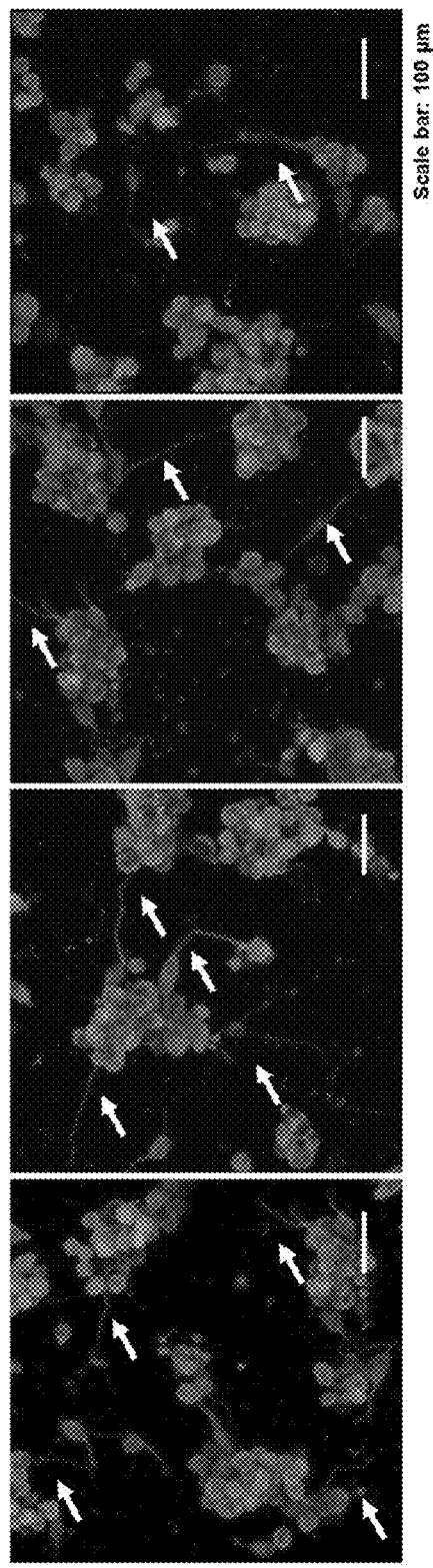
FIG. 15C is the high magnification observation of many neurites outgrows of Neuro2a cells in GelGOMA Hydrogel (arrows pointing to neurites) at high magnification.

The advantage of the hydrogel disclosed herein refers to support for electrosensitive tissue regeneration. Myoblast cells (C1C12) and neuroblast cells (Neuro2a) are electrosensitive cells of muscles and neuron tissues exemplified in this disclosure. The mechanical and electroconductive properties of GelGOMA enable differentiation and maturation of these cells into muscles and neuron tissues evidenced by the expression of myotubes and neurite outgrowth in C1C12 and Neuro2a respectively as shown in FIG. 15A-C.

EXAMPLES

[Example 1] Fabrication of SF Nanofiber

The silk cocoons from Bombyx mori were degummed and the degummed silk was hydrolyzed by 40% (v/v) $H_2SO_4$ at 60° C. for 2 h under constant stirring. The hydrolysis reaction was terminated by 5-fold dilution with DW and washed repeatedly by centrifugation at 10,000 rpm until a neutral pH was achieved. After hydrolysis, the obtained water-insoluble silk fibroin was suspended in distilled water (DW) at 0.1% (w/v). Afterward, it was mechanically digested over an iced bath by ultrasonic homogenizer via a homogenizer probe (f=13 mm) operated at 300 W and 19.5 kHz for 15 min. The homogenization was repeated three times to obtain a milky liquid of SF nanofiber solution. After mechanical disintegration, the defibrillated silk fibroin was obtained by centrifugation at 4000 rpm for 15 min. The SF nanofiber dispersion in DW was kept at 4° C. until further use. The SF nanofiber can be used as a nanofiller to further potentiate the mechanical properties of the ultra-strong hydrogel.

[Example 2] Methacrylation of Gelatin

Functionalization of natural polymers even though rare is very important to achieve a tunable hydrogel. In this present disclosure, natural and widely researched gelatin biopolymers were covalently modified by methacrylates. To achieve a comparative study with general hydrogel and ultra-strong hydrogel disclosed in this study, singly methacrylated gelatin was included in this disclosure. The singly methacrylated gelatin (GelGMA) via GMA was produced. Wherein gelatin was dissolved in DW at 50° C. under constant stirring to make a 2% (w/v) gelatin solution. Then, methacrylated with 10 mL of GMA for 24 h. The GelGMA solution was post-processed by dialysis against DW at 40° C., froze at −80° C., and lyophilized for 3 days before storing at −20° C. until further use.

Described herein is the first step to the fabrication of ultra-strong hydrogel which is the synthesis of double methacrylated gelatin (GelMAGMA). GelMA was first synthesized by reacting 7 mL methacrylate anhydride (MA) with a 3% (w/v) gelatin solution prepared in DW at 50° C. The MA was added slowly under constant stirring to ensure proper mixing due to MA's hydrophobic nature. After 3 h of the first methacrylation, the pH of the solution was adjusted to 3.5 with 1 M HCl before the addition of 10 mL GMA and the reaction was continued at 50° C. under constant stirring for 24 h. The second methacrylation was finalized by dialysis of GelMAGMA against DW via dialysis membrane of 12-14 kDa, for 7 days in a shaking incubator at 40° C. The purified GelMAGMA solution was frozen, lyophilized for 3 days, and stored at −20° C. until further use.

[Example 3] Carboxylation and Carbodiimidation Reactions

The synthesis of GelMAGMA-GO biocomposite (Gel-GOMA) is an extension of the aforementioned method for GELMAGMA before purification by dialysis. Prior to the completion of GelMAGMA second methacrylation, carboxylation of GO was initiated by sonicating 1, 2, or 3 mg/mL GO (Fine Chemicals, S. Korea) suspension prepared in 5 mL DW for 1 h.

Then, 1.2 g of sodium hydroxide (NaOH) and 1 g of chloroacetic acid ($ClCH_2COOH$) were added to each GO suspension under continuous sonication for 3 h. The resulting carboxylated GO (GO-COOH) solutions were washed by repeated suspension in DW and centrifugation. The GO carboxylation is to increase the reacting sites of GO binding to GelMAGMA via carboxyl-amino conjugation. Thus, all hydroxyl functional groups on GO were converted to carboxyl groups for this conjugation.

Activation of the carboxyl group of GO-COOH was started by the addition of 2 mg/mL N-hydroxysuccinimide (NHS) and 4 mmol/L of 1-ethyl-3-(3-(dimethylamino)propyl)-carbodiimide hydrochloric acid (EDC) to GO-COOH solutions under constant stirring in the dark. The reaction was left overnight before termination with mercaptoethanol. Carbodiimidation reaction between activated GO-COOH (1, 2, and 3 mg/mL) solutions and unpurified GelMAGMA was concluded by mixing equal volumes of both reactants in a round bottom flask for 24 h under constant stirring. The conjugated GelMAGMA and 1, 2, or 3 mg/mL GO-COOH solutions are hereinafter referred to as GelGOMA 01, GelGOMA 02, or GelGOMA 03 respectively. Finally, the GelGOMA solutions were dialyzed against warm water at 40° C. in a shaking incubator for 7 days. The dialyzed solutions were filtered with miracloth, centrifuge to remove aggregates, frozen, freeze-dried, and stored at −20° C.

[Example 4] Characterization of Hydrogels

To confirm the methacrylation of GelGMA, double methacrylation of GelMAGMA, and carbodiimidation of Gel-GOMAs, proton nuclear magnetic resonance ($H^1$-NMR) at 400 MHz with Bruker DPX FT-NMR Spectrometer (9.4T) of Bruker Analytik GmbH company was performed. Using deuterium ($D_2O$), 5 mg/ml sample solutions were prepared from GelGMA, GelMAGMA, and GelGOMAs sponges. All sample solutions were filtered with a 0.45 pin syringe filter before analyses.

ACD/NMR Processor software was used for baseline correction before the measurement of spectra of interest. The covalent binding of GMA to gelatin was confirmed with the appearance of methacrylate vinyl and methyl peaks which are higher in double methacrylated groups. Also, the disappearance of lysine peaks was noticeable and significantly reduced in double methacrylated groups. The graft copolymerization reactions that occurred in the fabrication of GelGMA, GelMAGMA, and GelGOMAs sponges were studied with Frontier PerkinElmer. While surface morphologies of fabricated sponges were observed with field-emission (SEM) For the FT-IR, samples were prepared by grinding with potassium bromide before obtaining the FT-IR spectra, while gold/palladium-coated samples were used to obtain the SEM micrograph.

Reduction of GO-COOH confers electroconductivity properties on the fabricated hydrogel. Therefore, gold/palladium coated samples were used for the EDX mapping to determine the percentage reduction of GO-COOH upon covalent linkage to GelMAGMA. The appearance of amides I, II, and III affirmed the graft copolymerization in the FT-IR spectra (See FIG. 2A).

The tests samples were grouped into sponges+GO solutions group comprising GO, GelGMA+GO, SGMA+GO, and GelMAGMA+GO; sponges+GO-COOH solutions group comprising GO-COOH, SGMA+GO-COOH, GelGMA+GO-COOH, and GelMAGMA+GO-COOH; lastly, GelGOMA varied concentration group comprising GelGOMA 01, GelGOMA 02, and GelGOMA 03.

In the first two groups, GO or GO-COOH were dispersed in DW to make a 2 mg/mL concentration, and SGMA, GelGMA, or GelMAGMA sponges were dissolved in it to make the concentration of 5 mg/mL. These groups involved the physical mixing of sponges with either GO or GO-COOH and are therefore referred to as physical mixture groups. Both GO and GO-COOH at 2 mg/mL concentrations without sponges were included as a control. The GelGOMA varied concentration group is referred to as the chemical group because of the covalent linkage of GO-COOH to GelGOMA through carbodiimidation reaction. Chemical group solutions were prepared by dissolving GelGOMA 01, GelGOMA 02, or GelGOMA 03 sponges in DW at 5 mg/mL concentration. All the solutions were transferred to a glass vial and observed at ambient temperature, and sample images were taken at intervals (See FIG. 3).

The present disclosure provides a bioink with/without cells that is photopolymerizable in a DLP printer. Having singly of doubly methacrylated, the various synthesized bioinks become photocurable in the presence of a photoinitiator, therefore suitable for DLP printer for hydrogel fabrication. In this disclosure, lithium phenyl-2,4,6-trimethylbenzoylphosphinate (LAP) was used as a photoinitiator for the fabrication of both cellular and acellular hydrogel. For the acellular hydrogel fabrication, 0.3% (w/v) LAP solution was made in phosphate buffer saline. Thereafter, methacrylated sponges were completely dissolved in the 0.3% (w/v) LAP solution to make 10, 20, or 30% (w/v) bioinks via a planetary vacuum mixer and kept briefly at 40° C. In this disclosure, hydrogel concentrations are named after the concentration of bioink from wherein they are fabricated. The concentration of LAP and bioink is optional and dependent on the application and other factors. The dissolved bioinks were filtered through a 40 μm nylon-mesh cell strainer to remove debris.

For the cell encapsulated hydrogels, 0.3% (w/v) LAP solution was prepared in serum-free DMEM under sterile conditions. The LAP solution was filtered with a 0.22 μm syringe filter before dissolving the methacrylated sponges via a vacuum mixer. Sponge debris were removed with a cell strainer and the bioink was pasteurized at 60° C. for 30 min.

[Example 5] Fabrication and Properties of Hydrogels

The photopolymerization of bioinks was carried out with a DLP printer using a UV source at 365 nm which is biofriendly. Desired computer-aided designs (CADs) models were imported as stereolithography (STL) files to the bioprinter's slicer software before exporting them to the DLP printer. Printing parameters were selected to obtain a good hydrogel structure. In this study, the printing parameters used for GelGOMA hydrogel fabrication are presented in table 5.

TABLE 5

| | DLP printing parameters | | | |
|---|---|---|---|---|
| | Layer thickness | Base layer curing time | Curing time | Ultraviolet light power |
| GelGOMA | 50 μm | 2.5 sec | 2.5 sec | 4.79 mW cm$^{-2}$ |

In some cases, the printing parameters can be varied to obtain maximum results and it is dependent on the nature of bioinks among other factors. The bioink was introduced to the bioprinter vat to begin layer-by-layer automated photopolymerization. After printing, hydrogels were rinsed with PBS to remove uncured bioink. It should be appreciated that the DLP printer is a potent tool to ensure the repeatability of designed structures. The complex structure printability of GelGOMA bioink was investigated with a customized DLP printer. Micro and nano-size complex structures, such as microporous scaffolds, thinker of Rodin, DNA double helix, meter rule, and human hand, were modeled with SolidWorks and the CAD transferred to the DLP printer as an STL file. A 25% (w/v) photocurable GelGOMA bioink was used to print all structures as described earlier (See FIG. 12). The 3D constructs demonstrated robust mechanical properties and structural integrity. One of the characteristics of this present disclosure is the mechanical strength of the hydrogel. Confirmation of improved strength, elasticity, and biocompatibility of GelGOMA reported in this disclosure was done by physical characterization of the printed hydrogel. The rheological properties of ultra-strong hydrogels were determined with Anton Paar MCR 302. The rheometer was equipped with a Peltier element, thermostatic hood, and sandblasted-type geometry (PP25, 25 mm diameter).

Viscoelastic analyses were performed on disc-shaped hydrogel samples of diameter 25 mm and thickness of 2 mm. From the frequency sweep measurements, dynamic moduli were obtained at a frequency range of 0.1 to 100 rad/s while keeping the shear strain constant at 1%. A universal testing machine (UTM) equipped with a 10 kgf load cell was used to obtain stress-strain curves and cyclic stress-strain curves. For the compressive test, 8 mm diameter (d) and 10 mm thickness (t) hydrogel discs were obtained from a DLP printer and compressive force was applied to each hydrogel at 10 mm/min velocity until it breaks.

On the other hand, a dog bone shape hydrogel with a concave column of 15 mm length (l), 10 mm width (w), and 2 mm t was subjected to a tensile jig at a stretch velocity of 10 mm/min until the sample breaks to determine the tensile strength. Cyclic compressive and tensile tests were conducted at 100%, 90%, and 80% of the maximum strain, and loading-unloading cycles were performed 10 times for each hydrogel sample at a velocity of 50 mm/min. All hydrogel samples for mechanical and rheological analyses were printed from 10, 20, or 30% (w/v) bioinks via a DLP bioprinter as described.

While GelGOMA hydrogel provides a solution to the conventional hydrogel's limitation, we further explore the possibility of improving GelGOMA physical properties, 0.1% (w/v) SF nanofibers were added to GelGOMA 02 photocurable solution before DLP printing to give GelGOMA_SF hydrogel. Tests were carried out immediately after hydrogels printing at 80% humidity and ambient temperature. Furthermore, the ability of the hydrogel to withstand sudden load impact was tested with the iron beads drop test. Wherein, 500 g iron bead was dropped from 10 cm to a 7×4×0.3 cm (l×w×t) 30% (w/v) GelGOMA_SF hydrogel fixed on a jig. Additionally, a 1 cm diameter bead of 30% (w/v) GelGOMA_SF hydrogel was dropped from 30 cm height to a smooth surface to check the elasticity of the ultra-strong hydrogel. A high-speed camera was used to record the bouncing of the iron bead and hydrogel bead from a fixed distance. Visual analyses of hydrogel strength, elongation rate, resilience, and rebound height of GelGOMA and iron beads were performed.

[Example 6] Degradation of Hydrogels

The possible application of the ultra-strong hydrogel for the engineering of strain-bearing tissue necessitates the analysis of its biodegradability. Using a DLP printer, hydrogel discs of 10 mm diameter and 4 mm thickness were produced from 10, 20, or 30% (w/v) GelGOMA 02, GelMAGMA, and GelGMA bioinks. Triplicate samples of each hydrogel were incubated in 2 U Pronase E solution prepared in PBS at 37° C. in a shaking incubator for 30 days.

[Example 7] the Electrical Property of the Hydrogel

A 4-probe measurement was used to eliminate electrical resistance due to the current flow and contact of the connection. The hydrogels used were SGMA, GelGMA, GelMAGMA, and GelGOMA, at 10%, 20%, or 30% concentrations. The distance of the electrodes penetrating the hydrogel is 1 mm. An I-V sweep test was performed using the 4-point probe method. First, the four external electrodes at both ends were connected 1 mm deep into the hydrogel test sample, and then a current sweep was performed from −0.01 A to 0.01 A in $5×10^{-5}$ A steps, and the voltage was measured by connecting the central electrode. The I-V sweep was measured using a Keithley 4200-SCS parameter analyzer, and the DC voltage was used to check the resistance value for each material. To increase the reliability of the current sweep test data, a frequency sweep test at AC voltage was performed.

Voltage and current were controlled using a Keithley 4200-SCS parameter analyzer, and conductance was measured by sweeping the frequency between 20 Hz and 200 kHz in 1000 Hz steps for each measurement with an Agilent 4284 LCR Meter. At this time, the signal level was set to 0.4 V, and it was measured by the 2-prove method by connecting all four electrodes except for the central probe on both sides, unlike when measuring I-V.

Figure 13:
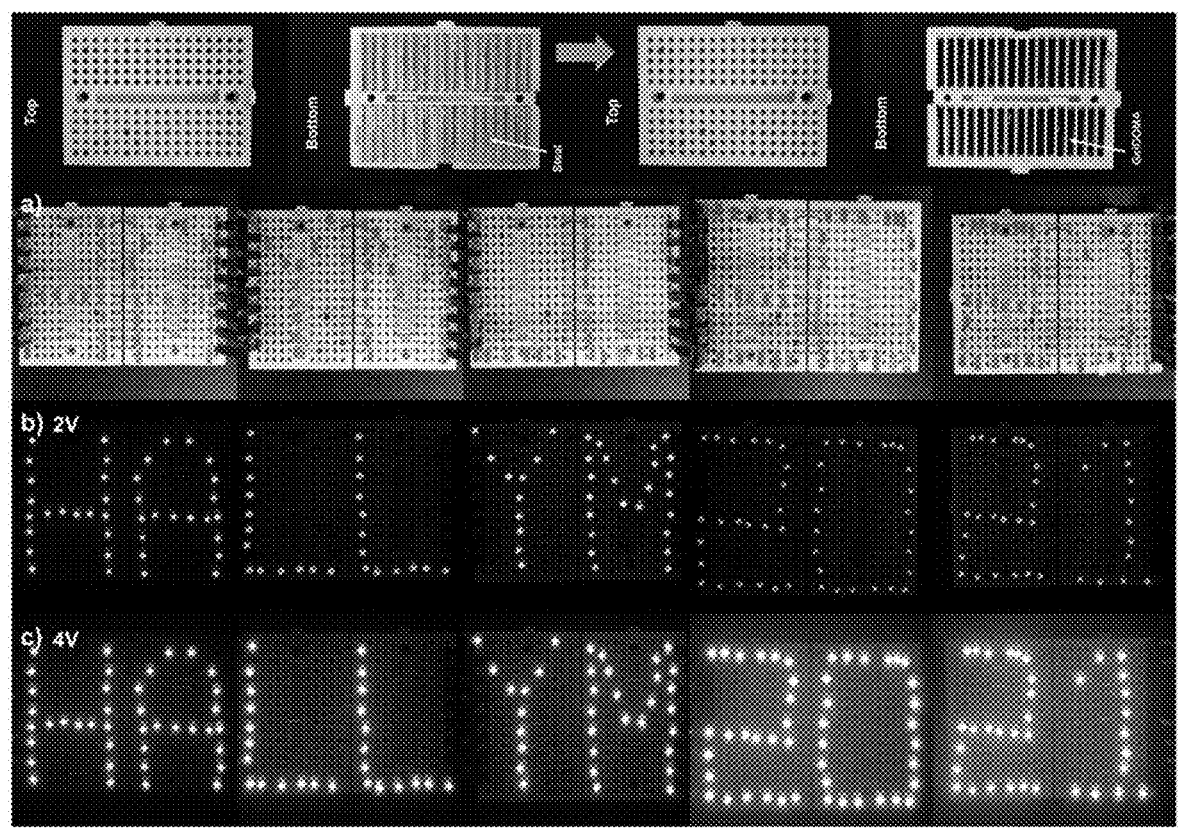
FIG. 13 is LED lighting using GelGOMA as a conductive hydrogel. (A) Representative digital images of a breadboard with the conductive steel replaced by GelGOMA hydrogel to light a specially arranged LED bulb to form HALYM2021. (B) Specially arranged LED lighting at 2 V representing low voltage displays low-intensity light. (C) Specially arranged LED lighting at 4 V represents high voltage and displays high-intensity light.

We display the significance of the electrical conductivity of GelGOMA with light-emitting diode (LED) lightning using a solderless mini breadboard. The electrically conductive metal clips in the breadboards were replaced with GelGOMA hydrogel printed from its 25% (w/v) bioink. LEDs were fixed to the breadboards in an arranged pattern and potential differences at 2 V or 4 V were applied in the darkroom (See FIG. 13).

[Example 8] Biocompatibility of Hydrogels

Another embodiment of this disclosure is the biocompatibility of hydrogel. The cytocompatibility and cellular proliferation potentials of ultra-strong hydrogel and its eluate were analyzed with human dermal fibroblast (HDF) cells.

HDF cells were seeded in high glucose Dulbecco's modified Eagle medium (DMEM) completed with 10% (v/v) fetal bovine serum (FBS) and 1% (v/v) penicillin-streptomycin (P/S). Hydrogel biocompatibility effects on both 2D and 3D cell cultures were investigated. For the 2D cell cultures, 2 mL of 25% (w/v) photocurable GelGMA, GelMAGMA, and GelGOMA02 were prepared in 6-well plates and UV treated for 10 sec. Then, 10 mL of complete DMEM was added to each hydrogel and incubated in a 5% $CO_2$ incubator at 37° C. After 72 h incubation, the hydrogel eluates were harvested and sterilely filtered for 2D HDF cell culture. Thereafter, HDF cells were seeded in a 24-well plate at 5000 cells/well with complete DMEM. After cell attachment, the culture media were replaced with 200 μm of hydrogel eluates and the culture continued for the next 24 h. The cell viabilities were examined with a CCK-8 assay according to the manufacturer's protocol. Concomitantly, real-time cell proliferation for 24 h was observed under a bright-field (BF) and green-fluorescent field (Fluorescein isothiocyanate; FITC) via INCELL 2200 imaging system. For the fluorescent imaging, HDF cells were labeled with PKH67 dye. Labeled/unlabeled HDF cells were seeded in 6-well plates at a concentration of 10,000 cells/well. The culture media were changed to hydrogel eluates of respective samples before incubation in the INCELL culture chamber for 24 h. Analyses were performed by INCELL developer software.

Figure 14A:
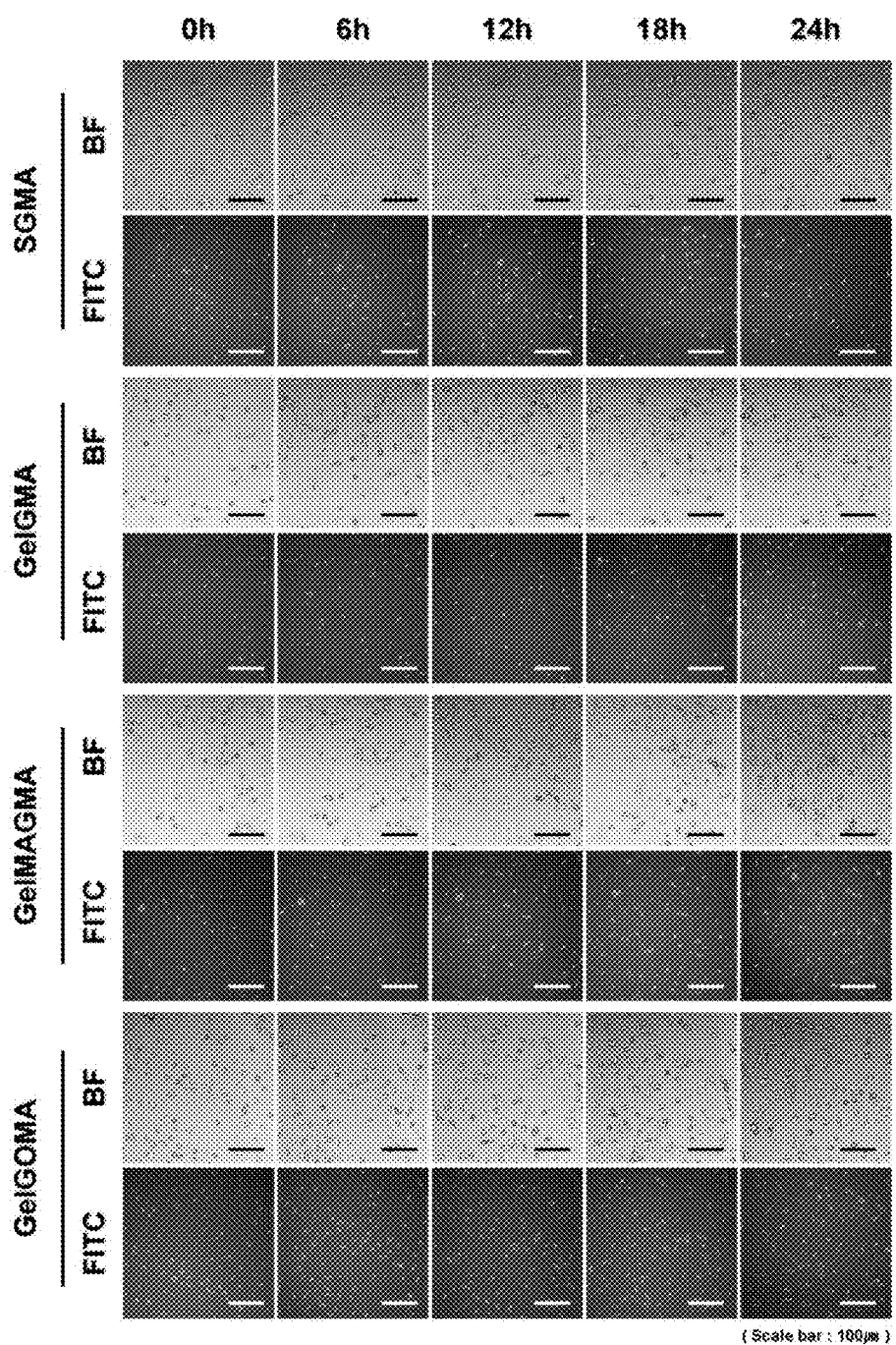
FIG. 14A shows images of Human dermal fibroblast (HDF) cultured in GelGOMA hydrogel eluate for real-time proliferation monitoring. Cell proliferation was observed by labeling human dermal fibroblast cells with PKH67 for FITC and unlabeled HDF with a bright field (BF).
Figure 14B:
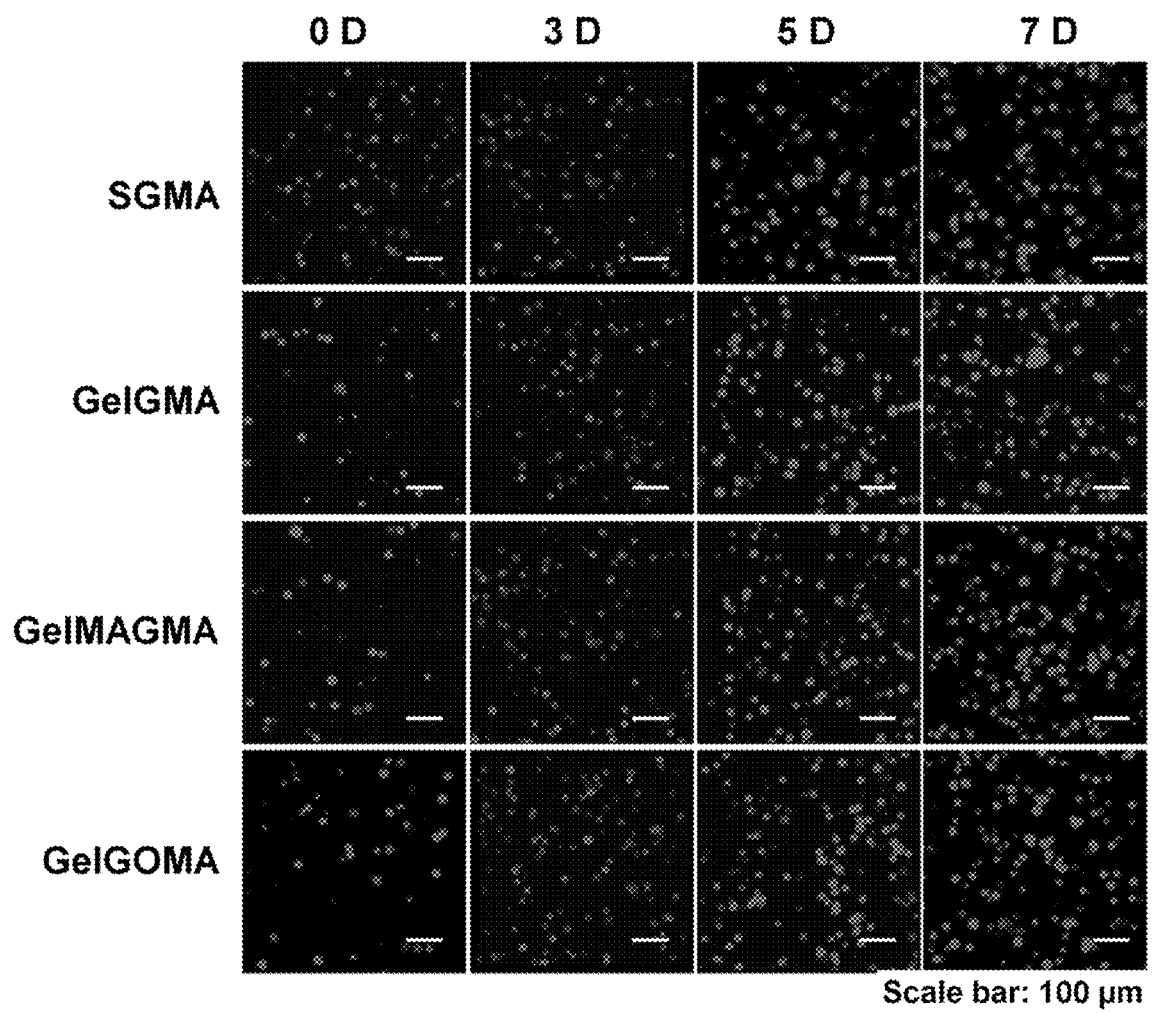
FIG. 14B shows the viability of HDF inside GelGOMA hydrogel as observed with a confocal microscope.
Figure 14C:
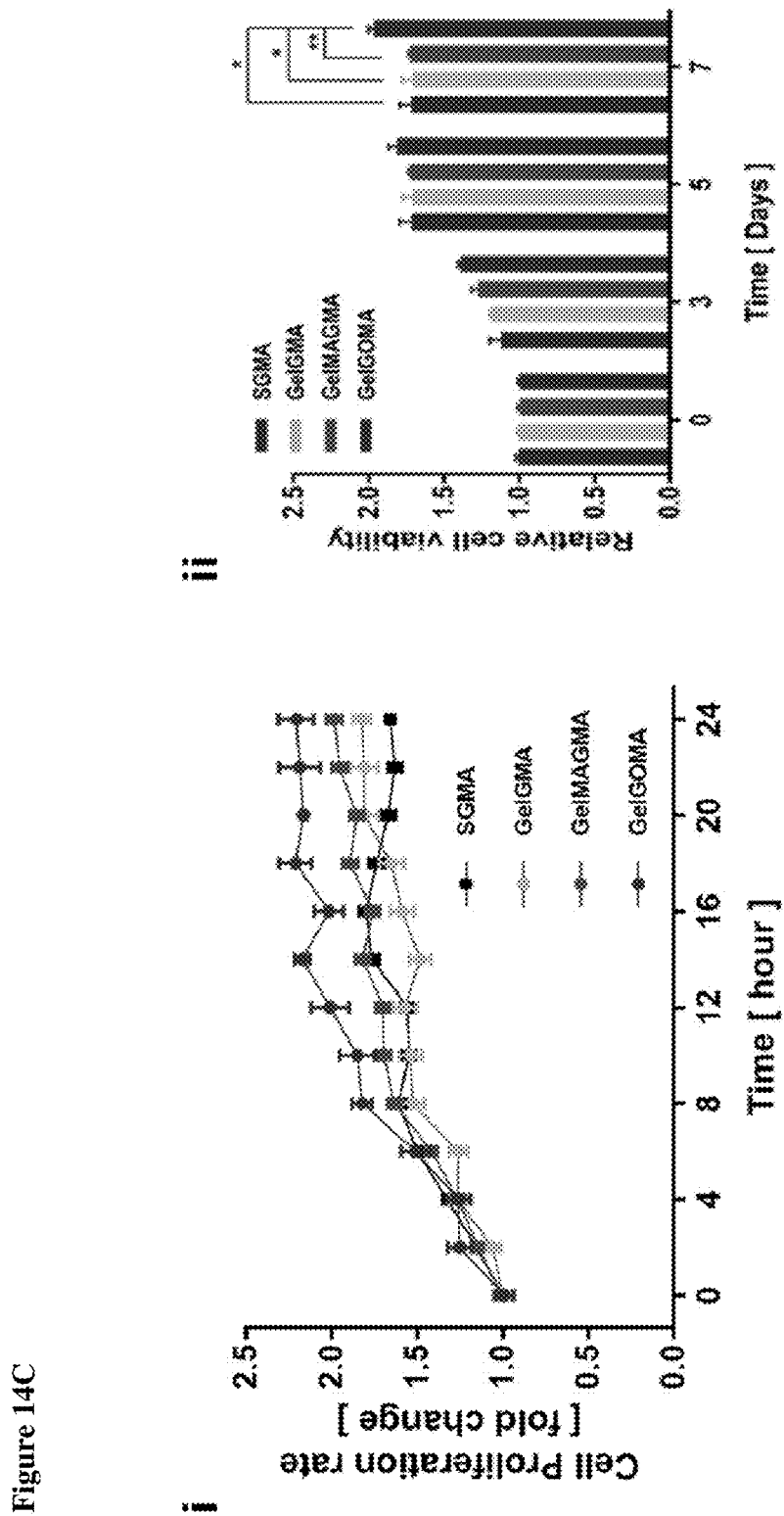
FIG. 14C shows the quantification of HDF proliferation and GelGOMA cytocompatibility. (i) Cell number counting results in real-time GelGOMA hydrogel eluate testing. (ii) CCK-8 assay of hydrogel encapsulated HDF to affirm cytocompatibility of GelGOMA.

For the 3D cell culture, HDF cells were encapsulated in 25% (w/v) GelGMA, GelMAGMA, and GelGOMA hydrogels via 3D DLP bioprinting. Briefly, HDF cells at passages 4-5 were detached using 0.25% trypsin-EDTA, counted, and resuspended in respective bioinks at $1×10^6$ cells/mL concentration. The bioinks were prepared from GelGMA, GelMAGMA, and GelGOMA sponges dissolved in LAP (0.3% w/v) containing serum-free DMEM at 25% (w/v) concentration under sterile conditions as described earlier. Afterward, the cell-loaded bioink solutions were introduced into the DLP bioprinter under sterile conditions. Cell encapsulated printed architectures were cultured for 7 days in completed DMEM under standard cell culture conditions. Samples were harvested at specific time intervals. Per manufacturers' protocols, cytotoxicity, and proliferation of encapsulated HDF cells were evaluated via Live/Dead and CCK-8 assay kits, respectively. Samples were visualized with a confocal microscope (See FIG. 14).

[Example 9] Electrosensitive Cells Differentiation and Whole-Mount Hydrogel Immunofluorescent Staining To investigate the effect of electroconductivity of GelGOMA on the differentiation of electrosensitive cells, immortalized mouse myoblast (C2C12) and neuroblast (Neuro2a) cells were purchased from Koram Biotech.

High glucose DMEM supplemented with 10% (v/v) FBS and 1% (v/v) P/S was used as growth media for C1C12 while high glucose DMEM supplemented with 1% (v/v) P/S, 1% (v/v) nonessential amino acid (NEAA), 1% (v/v) sodium pyruvate (NaPyr), and 10% (v/v) FBS was used for N2a growth media. C2C12 and Neuro2a were encapsulated in GelGOMA as described above via a DLP printer. The cell-laden hydrogels were cultured in their respective growth media for 3 days. Afterward, the growth media were changed to differentiation media.

For the C1C12, the differentiation medium comprises low glucose DMEM, 2% (v/v) horse serum (HS; Gibco, Waltham, MA, USA) and 1% (v/v) P/S while the differentiation media for N2a comprises high glucose DMEM, 1% (v/v) P/S, 1% (v/v) NEAA, 1% (v/v) NaPyr, 1% (v/v) FBS, and 10 µM retinoic acid. Cell encapsulated hydrogels were harvested at intervals, gently washed in PBS, and fixed in 4% paraformaldehyde for 30 min. Whole hydrogels were permeabilized overnight at 4° C. in blocking buffer comprising 1×PBS, 5% (v/v) HS, and 0.5% (v/v) Triton X-100. Afterward, C1C12-laden hydrogels and Neuro2α-laden hydrogels were incubated overnight at 4° C. in myosin heavy chain 1 (MEW; 1:200) and α-tubulin (1:200) primary antibodies respectively. After several washing in PBS, DyLight® 550-conjugated (1:250) and FITC-conjugated (1:250) secondary antibodies were added to the hydrogels and counter-stained with DAPI (1:200). Stained hydrogel Images were immediately captured using a K1-fluo confocal laser scanning microscope (See FIG. 15).

The invention claimed is:

1. A preparation method of electroconductive and biocompatible hydrogel, the preparation method comprises:
    reacting a 3% (w/v) gelatin solution, prepared in distilled water at 50° C., with 7 mL of methacrylate (MA) anhydride, with constant stirring, to produce GelMA;
    reacting the produced GelGMA with 10 mL of glycidyl methacrylate (GMA), with dialysis against the distilled water via a dialysis membrane of 12-14 kDa in a shaking incubator at 40° C., to produce GelMAGMA; and
    reacting in carbodiimidation the produced GelMAGMA with carboxylated graphene oxide (GO-COOH), to produce GelGOMA.

2. The preparation method according to claim 1, wherein the reacting the GelMAGMA with the carboxylated graphene oxide (GO-COOH) comprises:
    preparing the carboxylated graphene oxide (GO-COOH) by reacting graphene oxide (GO) with 1.2 g of sodium hydroxide (NaOH) and 1 g of chloroacetic acid (ClCH$_2$COOH), with sonicating for one hour.

3. The preparation method according to claim 1, wherein the reacting the GelMAGMA with the carboxylated graphene oxide (GO-COOH) comprises:
    activating the carboxylated graphene oxide (GO-COOH) by adding 2 mg/mL of N-hydroxylsuccinimide (NHS) and 4 mmol/L of 1-ethyl-3-(3-(dimethylamino)propyl)-carbodiimide hydrochloric acid (EDC), with constant stirring.

* * * * *